United States Patent [19]
Schneider et al.

[11] Patent Number: 5,786,462
[45] Date of Patent: Jul. 28, 1998

[54] HIGH AFFINITY SSDNA LIGANDS OF HIV-1 REVERSE TRANSCRIPTASE

[75] Inventors: Daniel J. Schneider; Larry Gold, both of Boulder, Colo.; Juli Feigon, Los Angeles, Calif.

[73] Assignee: NeXstar Pharmaceuticals, Inc., Boulder, Colo.

[21] Appl. No.: 443,407

[22] Filed: May 17, 1995

Related U.S. Application Data

[63] Continuation of Ser. No. 238,863, May 6, 1994, Pat. No. 5,503,978, which is a continuation-in-part of Ser. No. 714, 131, Jun. 10, 1991, Pat. No. 5,475,096, which is a continuation-in-part of Ser. No. 536,428, Jun. 11, 1990, abandoned, and Ser. No. 964,624, Oct. 21, 1992, Pat. No. 5,496,938.

[51] Int. Cl.⁶ .................. C07H 21/04; C12Q 1/68; C12P 19/34
[52] U.S. Cl. .................. 536/23.1; 435/6; 435/92.1; 935/77; 935/78
[58] Field of Search .................. 435/6, 91.2; 935/77, 935/78; 536/23.1

[56] References Cited

U.S. PATENT DOCUMENTS

| | | | |
|---|---|---|---|
| 4,833,092 | 5/1989 | Geysen | 435/6 |
| 5,133,866 | 7/1992 | Kauvar | 435/6 |
| 5,270,163 | 12/1993 | Gold et al. | 435/6 |
| 5,475,096 | 12/1995 | Gold et al. | 536/22.1 |
| 5,496,938 | 3/1996 | Gold et al. | 435/6 |

FOREIGN PATENT DOCUMENTS

| | | | |
|---|---|---|---|
| 2 183 661 A | 6/1987 | United Kingdom . | |
| WO 89/06694 | 7/1989 | WIPO . | |
| 9214843 | 9/1992 | WIPO | 435/6 |

OTHER PUBLICATIONS

Arnold et al. (1992) Nature 357:85.
Baltimore (1970) Nature 226:1209.
Carey et al. (1983) Biochemistry 22:2601.
Davies et al. (1991) Science 252:88.
Gilboa et al. (1979) Cell 18:93.
Huang et al. (1990) J. Biol. Chem. 265:11914.
Irvine et al. (1991) J. Mol. Biol. 222:739.
Jaeger et al. (1989) Proc. Natl. Acad. Sci. USA 86:7706.
Kedar et al. (1990) Biochemistry 29:3603.
Kohlstaedt et al. (1992) Science 256:1783.
Kopp et al. (1991) Nuc. Acids Res. 19(11):3035.
Krug and Berger (1991) Biochemistry 30:10614.
Lowary and Uhlenbeck (1987) Nucleic Acids Res. 15:10483.
Jocobo–Molina et al. (1993) Proc. Natl. Acad. Sci. USA 90:6320.
Marshall and Caruthers (1993) Science 259:1564.
Merluzzi et al. (1990) Science 250:1411.
Nakane and Ono (1990) Biochemistry 29:2841.
Pauwels et al. (1990) Nature 343:470.
Peliska and Benkovic (1992) Science 258:1112.
Schneider et al. (1993) FASEB 7:201.
Temin and Mizutani (1970) Nature 226:1211.
Tuerk and Gold (1990) Science 249:505.
Tuerk et al. (1992) Proc. Natl. Acad. Sci. USA 89:6988.
Yarus and Berg (1970) Anal. Biochem. 35:450.
Zuker (1989) Science 244:48.
Joyce (1989) Gene 82:83.
Joyce and Inoue (1989) Nucleic Acids Research 17:711.
Ellington and Szostak (1990) Abstract of papers presented at the 1990 meeting on RNA Processing, Cold Spring Harbor Laboratory, Cold Spring Harbor, NY, p. 226.
Kinzler and Vogelstein (1989) Nucleic Acids Research 17:3645.
Kramer et al. (1974) J. Mol. Biol. 89:719.
Levisohn and Spiegelman (1969) Proc. Natl. Acad. Sci. USA 63:805.
Levisohn and Spiegelman (1968) Proc. Natl. Acad. Sci. USA 60:866.
Oliphant et al. (1989) Mol. Cell Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:3203.

*Primary Examiner*—Stephanie W. Zitomer
*Attorney, Agent, or Firm*—Swanson & Bratschun LLC

[57] ABSTRACT

Methods are described for the identification and preparation of DNA ligands to the HIV-1 reverse transcriptase protein. Included in the invention are specific ssDNA ligands to HIV-1 reverse transcriptase identified by the SELEX method. Also included are ssDNA ligands that inhibit HIV-1 reverse transcriptase.

1 Claim, 26 Drawing Sheets

| | | SEQ ID NO: |
|---|---|---|
| 1 | 5'- CCCCTGCAGGTGATTTTGCTCAAGT - 35N - AGTATCGCTAATCAGGCGGAT -3'<br>[35N TEMPLATE OLIGO] | 1 |
| 2 | 5'- ATCCGCCTGATTAGCGATACT -3'<br>[UPSTREAM PCR PRIMER] | 2 |
| 3 | 5'- BBB-CCCCTGCAGGTGATTTTGCTCAAGT -3'<br>[BIOTINYLATED DOWNSTREAM PCR PRIMER AND DOWNSTREAM CLONING PRIMER] | 3 |
| 4 | 5'- CCGAAGCTTAATACGACTCACTATAGGGATCCGCCTGATTAGGGATACT -3'<br>[UPSTREAM CLONING PRIMER] | 4 |
| 5 | 5'- TTCACACAGGAAACAG -3'<br>[DNA SEQUENCING PRIMER] | 5 |

FIG. 1B

```
                    ATCCGCCTGATTAGCGATACT - [35N] - ACTTGAGCAAAATCACCTGCAGGGG
                                                                              SEQ ID NO.:
  5                            CAGG  CTCCT GAGTGAAGTGCGGACATGTACCNNNN            6
 24                         CGCCAGG  CCCCT GTAGTCGGGCGGAGTCANNNNNN               7
 30,109                   CGTATAGGT  CCCCT GCCGCTAAACAGCGCCGCGGTA                8
 66,83                     CTGCCA GT CCCCT GTAATTAGACGGAAACTCCTGT                9
 79                         CAGCAGT  CCCCT ATTCATGGGCCGCGGTTCATG                10
 89                      TAACGCCAGG  CCCCT GTAATAGTGCGGATCGACAG                 11
 93       GAGCTGTTGTACAGTGCAAGTGTAGCAGTT  CCCCT                                 12
101        GTATCTTTAGTACAAGTGCTCGGCAGCT   CCCCCAC                               13
114                         TCGCCAGT  CCCCT GTTTCAGCGCGGATATGACCAT              14
120                    GTATGGCTCTCAGCCCAGG  CCCCT GATACAGTCG                    15

7                    GAAGAGCGTGCTGT  CCCCT TA GG GTAATTGTCNNN                 16
 21                       ACGCGTGCTGC  CCCAT AACGGTGGCTTCAANNNNN                17
 71               GACAATGAGTCAAGTCGCGTGCT  CCCCT GCTGTTG                        18
 82              CGGGCCCCTGATTAACGCGCGCTG  CCCCT CGGGTG                         19
 90              CGATATGAGCGTGAGCGTGCTT   CCCT GTTGGTGN                         20
 95               GTCTGTCAGATTCATGCGTGCTC  CCCCT TCTGGTG                        21
 97                      CTGGAGCGTGCTG  CCCCT AAAGGTGACTTACCAAG                 22
102               TAGCTACACTATATGCGCGTGCTC  CCCCT GTTCGTG                       23
108             CTTGGCCCGTATTCGCGTGCTGTC  CCCCT GAGATG                          24
  6                        GAACGTGCAG  CCCCC GAAACGTGACTAGCAANNN                25
 37                    GGATTTTTGTGCAAG  CCCCC GAAAGCTGATNNNNN                   26
 10                    ACGT CAGGA CCCCT CATCGATTTTCTTAAGNNNNN                   27
```

FIG. 3A

| | | |
|---|---|---|
| 31 | TTAGCAAAGGAGCCCCCGGACTCAGATTACNNNNN | 28 |
| 65 | TGTTATAGTCCCCTGCCGCTGTTCTCGCGGGATTN | 29 |
| 100 | CAAGTCAAATCCCCTGACAGGAATTCCTTCCTGGA | 30 |
| 106 | TGTTCAGTCCCCCTCTCAAGCTACTTTACTTTGTA | 31 |
| | | |
| 25 | AGCGAGCTTATTAGAAGGATAAACCGCCTANNNNN | 32 |
| 74 | TGCTGGTCA TAGG TAAACAGCCCTGAGCTAACAGA | 33 |
| 77,105 | CAGAAGGATAAACTGTCCAGAACATGGAATATATC | 34 |
| 84 | ATCGAGGTGATCAGAAGGATAAACCGCCGGGGCCT | 35 |
| 28 | CTAAACGGTGAAGGGTCTTTGCAGATGAACAANNN | 36 |
| | | |
| 94 | TTAGCAAAG TAGAAGC CGGT TA GAAGACCTA GAAC | 37 |
| 113 | TTAGCAAAG TTGAAGC CGGACTAACAAGCTCTACG | 38 |
| 115 | GGGCTCAAGCTTGA GCGCGG CTCTC CACCTACG | 39 |
| | | |
| 19 | TGTCGGGTGGCTTTAGCAGAGACAATATGCATTNN | 40 |
| 26 | CTATAACCAGGTTTCGGGTGCTTTAGCAAANNNNN | 41 |
| 63 | GGGAGGGAGGGAGGGCCGTAGCTAATTAGGATCAA | 32 |

FIG. 3B

```
ATCCGCCTGATTAGCGATACT - [35N] - ACTTGAGCAAAATCACCTGCAGGGG
```

| | | SEQ ID NOS.: |
|---|---|---|
| 2 | ACGCGTGCTG CCCCTAAAGGCGATTGTCGGATGTT | 43 |
| 26 | TACGTGAGCGTGCTGTCCCCTAAAGGTGATACGTC | 44 |
| 31 | CTGGAGCGTGCTG CCCCTAAAGGTGACTTACCAAG | 45 |
| 33 | CCGGTGCTG CCCCTTAAGGTGATGGTGTATATTCC | 46 |
| 45 | TCTCCGACTCAAAGCGCGTGCT CCCCT CCGGTG | 47 |
| 12,21,46 | CGTATAGGTCCCCTGCCGCTAAACAGCGCCGCGGTA | 48 |
| 13 | GCCAGGTCCCCTGTAATTA GACGGAAACTACCTGT | 49 |
| 28 | GCCAGGACCCCTGTAATCT GGCGTATTTCCCTGTT | 50 |
| 38 | CGCCAGTACCCCTGTAAGTG GGCGGAAACTCTAGT | 51 |
| 41 | TCGTCAGGACCCCTGTAAACA GGCGGGATAATCTA | 52 |
| 14 | GGCCCCTCAGCTTGAGCGCGGACTACATATTATC | 53 |
| 15 | GGCCCCTCAGCTTGAGCGCGGAATCACTAAGATAC | 54 |
| 48 | GGCCCCTCAGCTAGAGC CGGATTAAACAGTCTTCA | 55 |
| 10,32 | TATTTGCCCTTGCAGGCCGCAGGAGTGCTAGCAGT | 56 |
| 6,18,20,23,27,35,40 | CAGGCGTTAGGGAAGGGCGTCGAAAGCAGGGTGGG | 57 |
| 5,43 | CAGGCGCC GGGG GGC TGGGAATACAGTGATCAGCG | 58 |
| 47 | CAGGCCTT GGGC GGGCCGGGACAATGGAGAGATTT | 59 |

FIG. 4A

|  |  | SEQ ID NOS.: |
|---|---|---|
| 8,17,22,30 | AGCCAGTCAAGTTAATGGGTGCCAT GCAGAAGCA | 60 |
| 3 | AATCGGCCTTGTTTCGGGGTGCTTTAGCAGAGGAA | 61 |
| 11 | CAGGGTGCCGCTCAATTCTGGGTGCCTT GCAGAAG | 62 |
| 42 | CCAGCGGTGGCATCACGCGGACTTACTCTAGCA | 63 |
|  |  |  |
| 4 | TTAGCAAAG TTGAAGC CGGACTAACAAGCTCTACG | 64 |
| 37 | CTAGCAGAG TAGAAGC CGGACGATATATCGATGAT | 65 |
| 19 | GGACTCCCAG TTGATGCGCGGTCTTTATCACCTCC | 66 |
| 34,36 | AAGCTCTTAG TTGATGCGCGGTCAAAATTTAAGCT | 67 |
| 7,39 | GAAGCTCTTTTAG T GATGCGTGGACCAGTCCCCTT | 68 |
| 44 | GGGCTCCAGCTTGA G CGG CGACTTAATTGGTTATT | 69 |
| 16 | GATATACTTATTA CTT CGCACGGCTAACCAGACC | 70 |
|  |  |  |
| 1,29 | CAGAAGGATAAACTGTCCAGAACTTGGAATATATC | 71 |
| 25 | CTCGAGGTGATCAGAAGGATAAACCGCCGGGGCCT | 72 |

FIG. 4B

```
                                    A
                                  A   C
                                  G   T
                                  A   T
                                  C   G
                                  C   G
                                  T   A                                      RT1
  A     C        AA        AAACTG   ATATATC|A     GA       AAA
G  TA  T|CAG   GGAT                          CTT     GCA      T
C  AT  AGTC    CCTA 5'                       GGG     CGT      C
   G    T       CG                      3' G      A       CCA
```

SEQ ID NO: 71
FIG. 5A

```
                                    G |A
                                  C     C                                    RT4
                                  A     T
                                  T     T
                                  C     G
                                  T     A
                                  C     G
                                  G     C
  C        T   AA          CTAACAA    AAAATCA       G
G  AAAG  TG   GC - CGGA                          CCT   C
   TT|TC  AT   CG    GCCT                        GGG
A         AG   A  C     A 5'                 3' G      A
              T   C
              T   T           SEQ ID NO: 64
              A G              FIG. 5B
```

```
                                                                        RT6
      A    C       T T A G G G A A G G G C G T C G A A A      G     G|A C T T G
  G  T A   T|C A G G C G                                 G C A G G  T G G       A
  C  A T   A G T C C G C                                 C G T C C  A C T       G
     G   T           C                                 A                  A A A A C
                     T                                 G
                5'  A                                  G
                                                       G
                                                       G 3'
                            SEQ ID NO: 57
                              FIG. 5C
```

```
        G A T
        T   T
        C   A                                                         RT10
        C  G
        G  C
        C  G
  5' A T C     A T A C T|T A T T T G            C   C    A G                   A
                        C C C T T G C A G G         G C     G A G T G C T    G
                    3' G G G G A C G T C C          C G     T T C A|T G A
                                            A     A    A G                C
                                            C     A

SEQ ID NO: 56
                              FIG. 5E
```

SEQ ID NO: 60

SEQ ID NO: 48

SEQ ID NO: 44

SEQ ID NO: 67

RT26
```
          A A
C C C C T      A G G T G A T
G G G G A      T C C A C T A
          C G
```
Fragment of SEQ ID NO: 44

FIG. 6A

RT1
```
        A A
T C A G      G G A T
A G T C      C C T A
        C G
```
Fragment of SEQ ID NO: 71

FIG. 6B

RT4
```
      T      A A
A G   T G       G C - C G G A
T C - A T       C G   G C C T
             A G
```
Fragment of SEQ ID NO: 64

FIG. 6C

RT8
```
        C A A
A G T       G T T A A T
T C A       C G A T T A
        T A G
```
Fragment of SEQ ID NO: 60

FIG. 6D

RT36
```
        A A
A T T T     G C T
T A A A     C G A
         A
```
Fragment of SEQ ID NO: 67

FIG. 6E

SEQ ID NO: 73

```
                                                          SEQ ID NO:
5'- GTCCC TGTTC GGGCG CCA-- ----- ---->  -3'  (DNA 18-mer)    74
3'- CAGGG ACAAG CCCGC GGUGA CGAUC UCUAA  -5'  (RNA 30-mer)    75
```
FIG. 10A
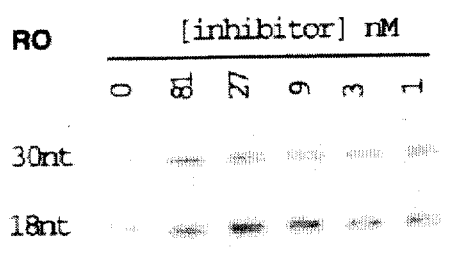
FIG. 10B
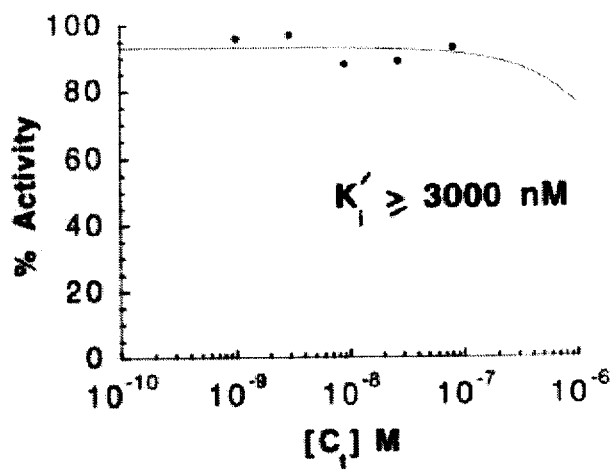
$K_i' \geq 3000$ nM
FIG. 10C
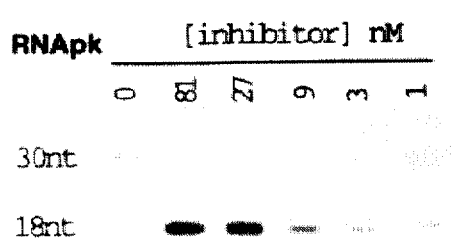
FIG. 10D
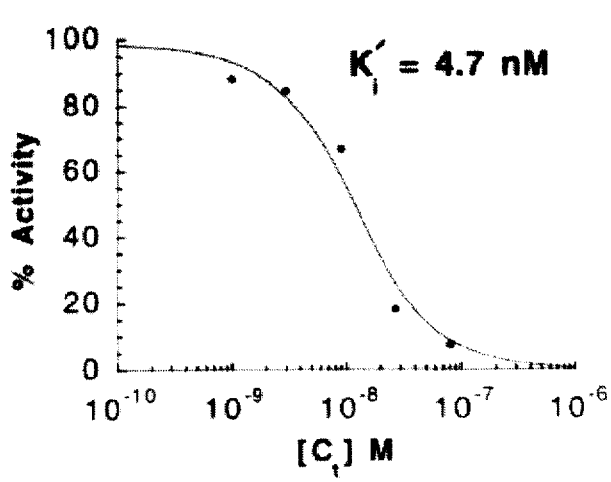
$K_i' = 4.7$ nM
FIG. 10E

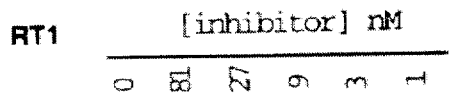
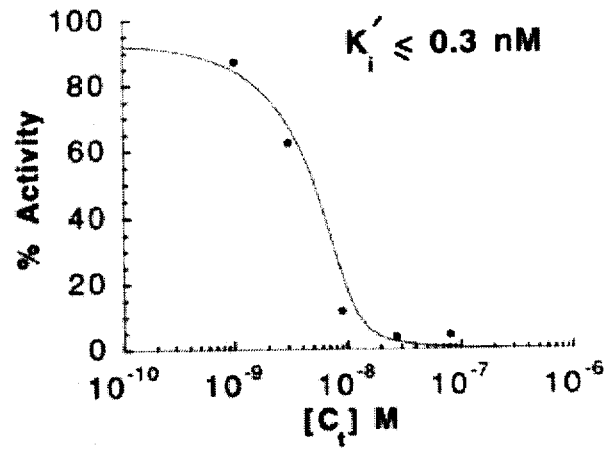
FIG. 10F
FIG. 10G
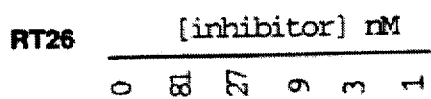
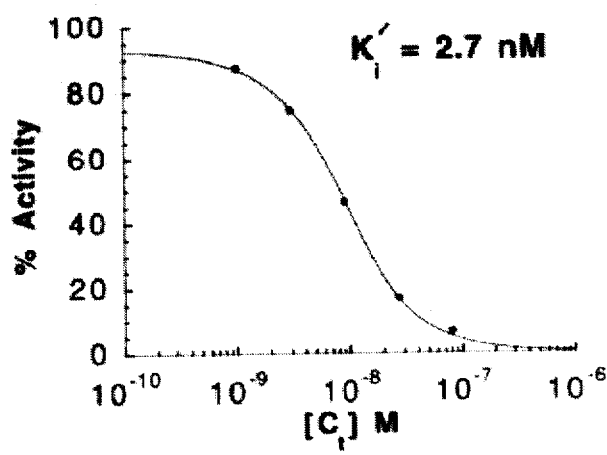
FIG. 10H
FIG. 10I

FIG. 11A

| FRAGMENT | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | SEQ ID NO: |
|---|---|---|---|---|---|---|---|---|---|---|---|---|---|---|---|---|---|---|---|---|---|---|---|---|---|---|---|---|---|---|---|---|---|---|---|---|
| RT1  | C | A | G | A | A | G | G | A | T | A | A | A | C | T | G | T | C | C | A | G | A | A | C | T | T | G | G | A | A | T | A | T | A | T | C | 71 |
| RT1A | C | A | G | A | A | G | G | A | T | A | T | A | G | T | C | T | G | T | C | T | A | A | C | T | A | C | G | G | C | T | A | C | G | T | C | 76 |
| RT1B | C | G | G | A | A | C | G | A | T | C | G | A | G | T | C | G | C | C | T | A | G | C | A | C | G | T | G | G | A | C | G | A | T | T | C | 77 |
| RT1C | C | G | G | A | A | A | G | A | T | A | T | A | C | T | G | T | C | C | C | G | G | G | A | A | C | A | C | G | T | T | T | G | T | T | C | 78 |
| RT1D | C | A | G | A | A | A | G | A | T | A | A | A | A | C | C | G | T | C | T | C | T | A | G | A | C | T | T | G | C | A | A | T | G | A | A | 79 |
| RT1E | C | G | G | A | A | G | G | A | T | A | T | A | C | T | G | T | T | T | C | T | A | G | A | A | C | T | T | G | C | A | G | T | C | C | A | 80 |
| RT1F | C | G | G | A | A | A | G | A | T | C | A | A | C | T | G | T | C | T | C | T | A | G | A | A | C | C | T | G | A | A | T | T | G | T | C | 81 |
| RT1G | C | A | G | A | A | G | G | A | T | A | A | A | C | T | G | G | G | G | A | C | A | G | A | C | C | T | T | G | C | A | T | C | G | T | C | 82 |
| RT1H | C | A | G | A | A | G | G | A | T | A | A | A | C | T | G | T | T | G | A | A | C | A | A | T | T | C | G | G | A | C | C | C | T | C | C | 83 |
| RT1I | C | G | G | A | A | G | G | A | T | A | A | A | C | T | G | T | C | T | C | T | A | G | C | A | A | T | T | C | G | C | A | C | T | C | C | 84 |
| RT1J | C | G | G | A | A | T | G | A | T | A | A | A | C | T | G | T | T | G | T | C | C | A | G | C | A | T | T | C | G | A | A | T | T | T | C | 85 |
| RT1K | C | A | G | A | A | G | G | A | T | A | A | G | G | C | T | T | G | C | C | C | T | G | A | A | C | A | G | C | T | T | T | G | A | G | G | 86 |
| RT1L | C | G | G | A | A | A | G | A | T | A | A | A | C | T | G | T | T | G | C | T | C | C | A | C | A | G | C | C | T | T | T | A | A | A | C | 87 |
| RT1M | C | A | G | A | A | G | G | A | T | A | A | A | C | T | G | T | C | C | C | C | T | A | G | A | C | C | T | G | A | A | A | T | T | T | C | 88 |
| RT1N | C | G | G | A | A | A | G | A | T | A | A | A | C | T | G | T | C | T | C | T | A | G | A | A | C | T | T | G | G | A | A | T | A | T | T | 89 |
| RT1O | C | A | G | A | A | G | T | A | T | A | A | A | C | T | G | T | C | C | C | C | A | C | G | A | C | G | C | G | G | A | A | A | T | G | C | 90 |
| RT1P | C | A | G | A | A | G | G | A | T | A | A | A | C | T | G | T | C | T | C | T | A | G | A | A | C | C | T | G | A | A | T | A | T | G | T | 91 |

FIG. 11A

```
A  C    NA  ANNCNGNNTNGNNCNNNGNNNNCNNN...
 TAT|CGG GGAN
GAT AGTC CCTA 5'
C   T CG
G        CG
         5    10   15   20   25   30   35
```

SEQ ID NO: 92

SEQ ID NO: 71

SEQ ID NO: 93

FIG. 12B

```
 A  C   AA    GGAT
G TA TCAG         A
C AT AGTC     CCTA
 G  T    CG
```

RT1t30

SEQ ID NO: 94

FIG. 12C

STEP 1
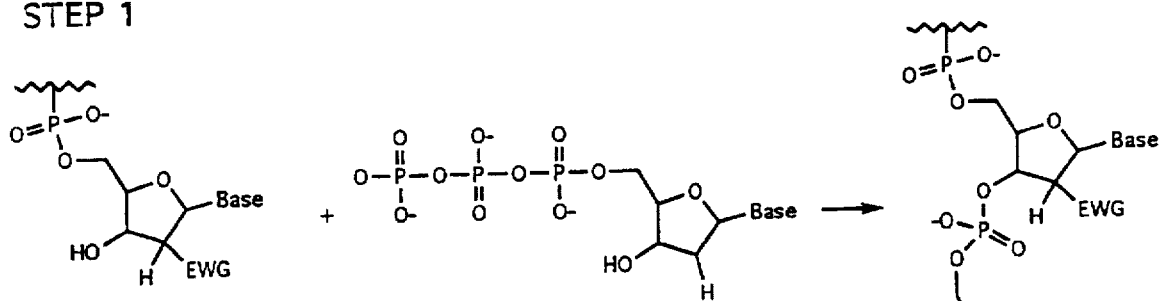
STEP 2
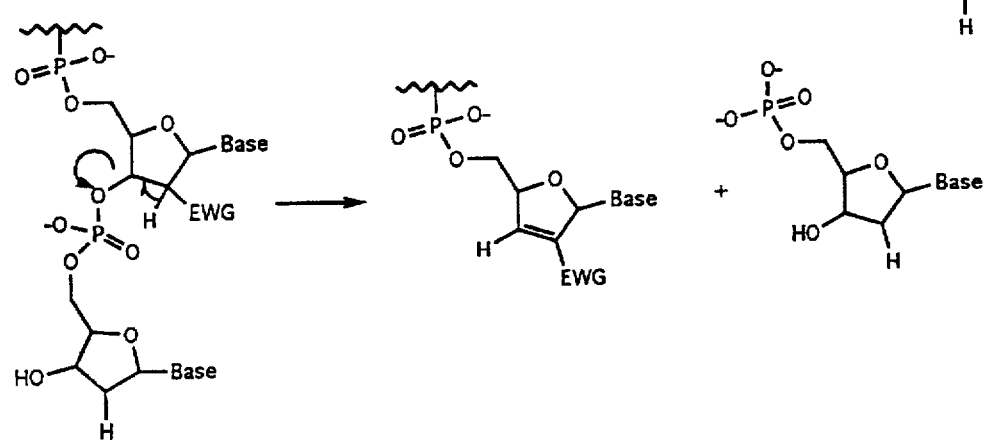
STEP 3
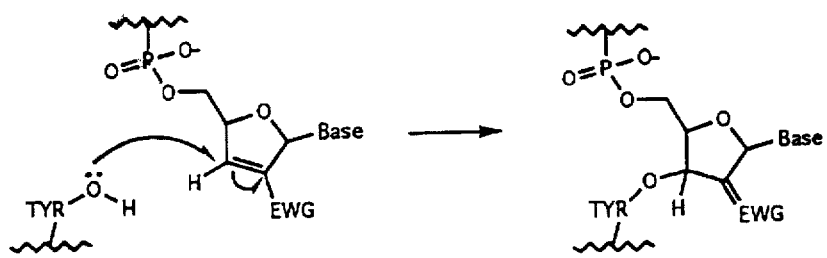
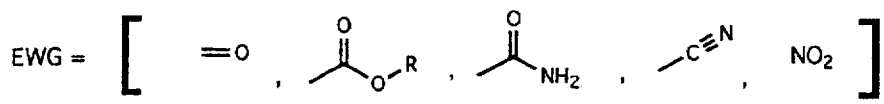
FIG. 15

HIGH AFFINITY SSDNA LIGANDS OF HIV-1 REVERSE TRANSCRIPTASE

RELATED APPLICATIONS

This application is a continuation of U.S. application Ser. No. 08/238,863 filed May 6, 1994, entitled "Method for Identification of High Affinity DNA Ligands of HIV-1 Reverse Transcriptase", now issued as U.S. Pat. No. 5,503,978. U.S. application Ser. No. 08/238,863 is a continuation-in-part of U.S. application Ser. No. 07/714,131 filed Jun. 10, 1991, entitled "Nucleic Acid Ligands", now issued as U.S. Pat. No. 5,475,096, which is a continuation-in-part of U.S. application Ser. No. 07/536,428 filed Jun. 11, 1990, entitled "Systematic Evolution of Ligands by Exponential Enrichment", now abandoned, and U.S. application Ser. No. 07/964,624, filed Oct. 21, 1992, entitled "Nucleic Acid Ligands to HIV-RT and HIV-1 Rev", now issued as U.S. Pat. No. 5,496,938.

This work was partially supported by a grant from the United States Government funded through the National Institutes of Health. The U.S. Government may have certain rights in this invention.

FIELD OF THE INVENTION

Described herein are methods for identifying and preparing high-affinity DNA ligands to HIV-1 Reverse Transcriptase (RT). The method utilized herein for identifying such DNA ligands is called SELEX, an acronym for Systematic Evolution of Ligands by EXponential enrichment. Specifically disclosed herein are high-affinity single-stranded DNA ligands. The invention includes high-affinity ssDNA inhibitors of HIV-1 RT. The invention also includes suicide inhibitors of HIV-1 RT.

BACKGROUND OF THE INVENTION

The reverse transcriptase (RT) of Type 1 Human Immunodeficiency Virus (HIV-1) plays an indispensable role in the life cycle of the virus. Its premier function is the synthesis of a double-stranded DNA copy of the RNA genome for integration into the host chromosome. This is achieved by the concerted application of a number of innate activities including minus-strand DNA synthesis via an RNA-dependent DNA polymerase activity, concomitant degradation of the template RNA strand via an RNase H activity, and plus-strand DNA synthesis via a DNA-dependent DNA polymerase activity (Baltimore, D. (1970) Nature 226:1209; Temin, H. M. and Mizutani, S. (1970) Nature 226:1211; Gilboa, E. et al. (1979) Cell 18:93–100; Peliska, J. A. and Benkovic, S. J. (1992) Science 258:1112–1118). Because the cells HIV-1 infects contain no endogenous RT, it must also possess a mechanism to ensure its packaging into the mature viral particle to guarantee its presence in the succeeding infection.

HIV-1 is generally accepted as the etiological agent of Acquired Immune Deficiency Syndrome (AIDS.). The importance of its function in the life cycle of HIV-1 and the lack of a natural function in the host cell make RT a preferred target for antiviral agents.

Several types of HIV-1 RT inhibitors are known. Many, such as AZT (3'-azido-2',3'-dideoxythymidine), are nucleoside analogs, which when incorporated into polynucleotides by HIV-1 RT, result in chain termination. (Kedar, P. S. et al. (1990) Biochem. 29:3603–3611; Huang, P. et al. (1990) J. Biol. Chem. 265:11914–11918). Other nucleoside analogs that inhibit HIV-1 RT include ddC (2',3'-dideoxycytidine) and ddI (2', 3'-dideoxyinosine). Inhibitors that are not nucleoside analogs have also been described. These include dipyridodiazepinones (e.g., Merluzzi, V. J. et al. (1990) Science 250:1411–1413; Kopp, E. B. et al. (1991) Nuc. Acids Res. 19(11):3035–3039), tetrahydro-imidazo[4,5,1-jk][1,4]-benzodiazepin-2(1H)-one and -thione (TIBO) derivatives (e.g., Pauwels, T. et al. (1990) Nature 343:470–474), and catechin derivatives (e.g., Nakane, H., and Ono, K. (1990) Biochem. 29:2841–2845). These non-nucleosides inhibit by mechanisms other than direct competition for substrate binding sites (Kopp, E. B. et al. (1991) Nuc. Acids Res. 19(11):3035–3039).

A family of phosphorodithioate-linked ssDNA nucleotides have been described with the property of inhibiting HIV-1 RT activity at $K_i$ values ranging from 0.5–180 nM (Marshall and Caruthers (1993) Science 259:1564–1570). The specific sequences of these nucleotides were based on the sequence of various nucleic acid substrates of HIV-RT.

RNA pseudoknots that bind specifically to the polymerase active site of HIV-1 RT and inhibit the RNA-dependent DNA polymerase activity have already been identified using SELEX (U.S. patent application No. 07/964,624, now issued as U.S. Pat. No. 5,496,938, which is specifically incorporated herein by reference; Tuerk, C. et al. (1992) Proc. Natl. Acad. Sci., U.S.A. 89:6988–6992).

The development of high affinity DNA ligands capable of inhibiting HIV-1 reverse transcriptase would be useful in the treatment of Type 1 Human Immunodeficiency Virus. Herein described are high affinity ssDNA ligand inhibitors of HIV-1 reverse transcriptase.

BRIEF SUMMARY OF THE INVENTION

The present invention includes methods of identifying and producing DNA ligands to HIV-1 RT and the DNA ligands so identified and produced. Specifically, ssDNA sequences are provided that are capable of binding specifically to HIV-1 RT. Included within the invention are the ssDNA ligand sequences shown in FIGS. 3 and 4.

Also included in this invention are DNA ligands of HIV-1 RT that are inhibitors of HIV-1 RT. Specifically, ssDNA ligands are identified and described which inhibit the RNA-dependent DNA polymerase activity of HIV-1 RT.

Further included in this invention is a method of identifying DNA ligands and DNA ligand sequences to HIV-1 RT comprising the steps of (a) preparing a candidate mixture of nucleic acids, (b) partitioning between members of said candidate mixture on the basis of affinity to HIV-1 RT, and (c) amplifying the selected molecules to yield a mixture of nucleic acids enriched for nucleic acid sequences with a relatively higher affinity for binding to HIV-1 RT.

More specifically, the present invention includes the ssDNA ligands to HIV-1 RT identified according to the above-described method, including those ligands listed in FIGS. 3 and 4. Also included are ssDNA ligands to HIV-1 RT that are substantially homologous to any of the given ligands and that have substantially the same ability to bind and inhibit HIV-1 RT. Further included in this invention are ssDNA ligands to HIV-1 RT that have substantially the same structural form as the ligands presented herein and that have substantially the same ability to bind and inhibit HIV-1 RT.

Further included in this invention are ssDNA ligands incorporating at specific positions nucleotide analogs possessing a reactive group able to covalently crosslink the ligand to HIV-1 RT upon binding. This invention also includes the ligands as described above, wherein covalent crosslinking is coupled to the activity of the HIV-1 RT.

The present invention also includes modified nucleotide sequences based on the DNA ligands identified herein and mixtures of the same.

BRIEF DESCRIPTION OF THE FIGURES

FIGS. 1A and 1B show the experimental design and oligonucleotide sequences used in generating the candidate mixture of ssDNA. A degenerate double-stranded DNA library was created using the Polymerase Chain Reaction to amplify oligo 1, using oligos 2 and 3 as primers. Box 1 shows the 35N template oligo (oligo 1) (SEQ ID NO: 1). Box 2 shows the upstream PCR primer (oligo 2) (SEQ ID NO: 2). Box 3 shows the biotinylated downstream PCR primer (oligo 3) (SEQ ID NO: 3) and downstream cloning primer (oligo 3 with biotins removed). Box 4 shows the upstream cloning primer (oligo 4) (SEQ ID NO: 4), and Box 5 shows the DNA sequencing primer (oligo 5) (SEQ ID NO: 5).

FIGS. 3A and 3B show sequences isolated from the library after cycle 12 (SEQ ID NOS: 6–42). The top of the Figure shows the upstream PCR primer (see FIG. 1B) and the complement of the downstream PCR primer and downstream cloning primer (see FIG. 1B). Only the 35 positions originally randomized are shown below for each numbered individual. However, the full-length sequence includes the upstream and downstream sequences as shown at the top of the Figure. Isolates were grouped and aligned by common primary sequence elements. Clones are indicated by number. Approximately 3 of 4 selected ligands contained the sequence CCCCT (boxed), or a variant of this pentamer. Other regions of similarity among isolates are shaded. Because these ligands were sequenced using a primer that annealed adjacent to the 35N region, often the sequence of the first few nucleotides at the 3' end was indecipherable. As the sequences of the unreadable regions are not necessary for this analysis, they are represented by "N"'s.

FIGS. 4A and 4B show sequences isolated from the library after cycle 15 (SEQ ID NOS: 43–72). The top of the Figure shows the upstream PCR primer (see FIG. 1B) and the complement of the downstream PCR primer and downstream cloning primer (see FIG. 1B). Only the 35 positions originally randomized are shown below for each numbered individual. However, the full-length sequence includes the upstream and downstream sequences as shown at the top of the Figure. Isolates were grouped and aligned by common primary sequence elements. Clones are indicated by number. Isolates were grouped and aligned by common elements. CCCCT, or a variant of this pentamer, is shown as boxed. Other regions of similarity among isolates are shaded.

FIGS. 5A–5H show the predicted secondary structures of eight individual ligands (RT1 (SEQ ID NO: 7), RT4 (SEQ ID NO: 64), RT6 (SEQ ID NO: 57), RT8 (SEQ ID NO: 60), RT10 (SEQ ID NO: 56), RT12 (SEQ ID NO: 48), RT26 (SEQ ID NO: 44), and RT36 (SEQ ID NO: 67)). The structure of each of the eight ligands in this figure include elements common to many other members of its respective group (boxed or shaded as in FIG. 4). The 35 positions originally randomized are demarcated by vertical lines.

FIGS. 6A–6E show the conserved internal loop motif. The sequence and predicted secondary structure of the internal loop motif of ligands RT26 (SEQ ID NO: 44) and RT1 (SEQ ID NO: 71) is illustrated, along with variants of the motif found in ligands RT4 (SEQ ID NO: 64), RT8 (SEQ ID NO: 60), and RT36 (SEQ ID NO: 67). The conserved loop sequences are indicated in boldface. The stems closing each side of the internal loop vary in both sequence and length.

FIGS. 10A–10E show the inhibition of RNA-dependent DNA polymerase activity of HIV-1 RT. The substrate for the inhibition assay is shown in FIG. 10A (SEQ ID NOS: 74–75). Extension reaction products are shown for R0 (degenerate ssDNA library), RNApk (RNA pseudoknot), RT1 (SEQ ID NO: 71), and RT26 (SEQ ID NO: 44) in FIGS. 10B, D, F and H. The $K_i$ plots are also shown in FIGS. 10C, E, G and I.

FIGS. 11A and 11B show the sequences of individuals isolated from the biased randomization SELEX of RT1 (SEQ ID NOS: 76–81). The 35N positions, aligned with the "wild-type" sequence of RT1 are shown in FIG. 11A. Positions absolutely conserved are indicated with an open circle, those partially conserved (fewer than three individuals possess a substitution) with a triangle, and those preferring a substitution with a bullet. Complementary sequences able to form secondary structure interactions are underlined. Predicted secondary structure of RT1 with a consensus sequence (suggested by the results of A) replacing the "wild-type" 35N region is shown in FIG. 11B (SEQ ID NO: 92). Only the upstream invariant region and 35N region are shown. Variable positions are represented with an N. The two preferred substitutions ($G_2$ and $T_{18}$) are indicated in boldface.

FIGS. 12A–12C show the predicted secondary structures of RT1 (SEQ ID NO: 71) and truncates (SEQ ID NOS: 93–94).

FIG. 15 shows the way in which covalent crosslinking is coupled to the activity of the enzyme. Step 1 shows the catalytic addition of a nucleotide triphosphate to a ligand that has a nucleotide analog at its 3' end containing an electron withdrawing group (EWG) at the 2' carbon. Step 2 shows the spontaneous elimination event whereby the newly added nucleotide is released and yields an electrophilic carbon at the 3' position of the sugar that is stabilized by the electron withdrawing group at the 2' position. Step 3 shows the formation of a covalent crosslink between the protein and the ligand.

DETAILED DESCRIPTION OF THE INVENTION

Figure 1A:
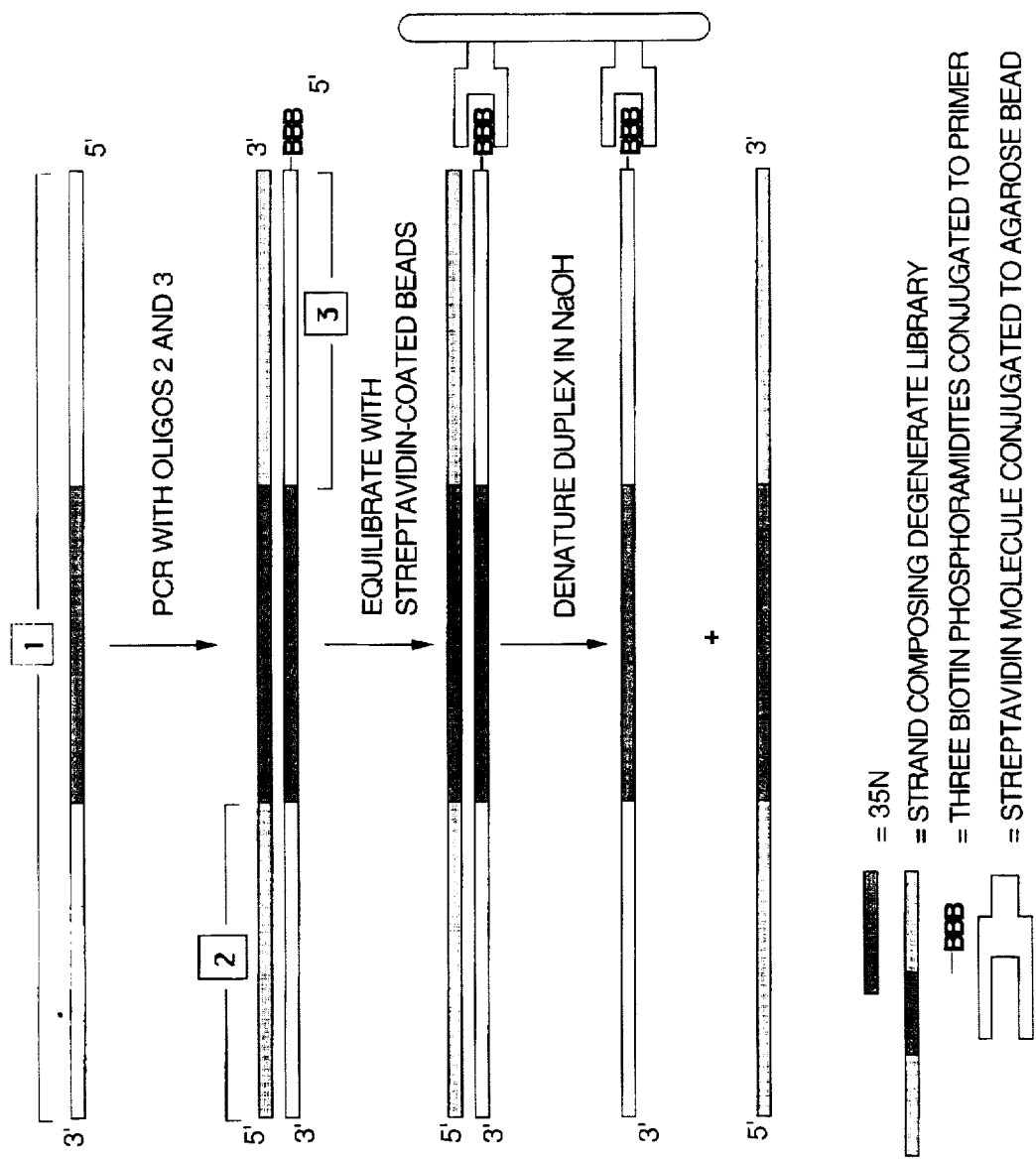

This application describes high-affinity DNA ligands to HIV-1 RT identified through the method known as SELEX. SELEX is described in U.S. patent application Ser. No. 07/536,428, entitled Systematic Evolution of Ligands by EXponential Enrichment, now abandoned, U.S. patent application Ser. No. 07/714,131, filed Jun. 10, 1991, entitled Nucleic Acid Ligands now issued as U.S. Pat. No. 5,475,096, U.S. patent application Ser. No. 07/931,473, filed Aug. 17, 1992, entitled Nucleic Acid Ligands, now U.S. Pat. No. 5,270,163 (see also WO 91/19813). These applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5-50%) are retained during partitioning.

4) Those nucleic acids selected during partitioning as having the relatively higher affinity to the target are then amplified to create a new candidate mixture that is enriched in nucleic acids-having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate an enriched candidate mixture. The SELEX Patent Applications also describe ligand solutions obtained to a number of target species, including both protein targets where the protein is and is not a nucleic acid binding protein.

SELEX provides high affinity ligands of a target molecule. This represents a singular achievement that is unprecedented in the field of nucleic acids research. The present invention applies the SELEX procedure to the specific target of HIV-1 reverse transcriptase (RT). In the Example section below, the experimental parameters used to isolate and identify the nucleic acid ligands to HIV-1 RT are described.

In order to produce nucleic acids desirable for use as a pharmaceutical, it is preferred that the nucleic acid ligand 1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

In co-pending and commonly assigned U.S. patent application Ser. No. 07/964,624, filed Oct. 21, 1992, now issued as U.S. Pat. No. 5,496, (No. '938), methods are described for obtaining improved nucleic acid ligands after SELEX has been performed. The No. '938 Patent, entitled Nucleic Acid Ligands to HIV-RT and HIV-1 Rev, is specifically incorporated herein by reference.

In the present invention, a SELEX experiment was performed in search of single-stranded DNA ligands with specific high affinity for HIV-1 RT from a degenerate library containing 35 random positions (35N). A large family was identified with an apparent affinity for HIV-1 RT about 700 times higher than the library from which they originated (described in Examples 1 and 2, infra). At least seven members of this diverse family, sharing little similarity with each other or with the RNA pseudoknot at the levels of primary and secondary structure, inhibit the RNA-dependent DNA polymerase activity of HIV-1 RT at very low concentrations, possibly competing with substrate for the polymerase active site by virtue of their higher affinity for RT (described in Example 2, infra). For at least one inhibitor this inhibition is specific for HIV-1 RT, as the polymerase activity of reverse transcriptases from Avian Myeloblastoma Virus (AMV-RT) and Moloney Murine Leukemia Virus (MMLV-RT) were unaffected by the presence of the inhibitory DNA ligand RT1t49(SEQ ID NO: 93). For one of the ssDNA inhibitors (RT1) (SEQ ID NO:), the importance of each selected residue was assessed by introducing an average of 9 new mutations (in the originally randomized region) and selecting for variants maintaining high affinity (described in Example 4, infra). Based on these results, we then removed 40% of the ligand and observed only a moderate loss of affinity. The 5' half of the truncate contained an internal loop motif common to other members of the selected library, likely creating a helix bend that provides a specific shape for direct contact by HIV-1 RT. The truncated ligand inhibited the polymerase activity of HIV-1 RT as well as the full-length ligand (see Example 4, infra), and binding of the truncate and the RNA pseudoknot were mutually exclusive (see Example 5, infra), suggesting they interact with HIV-1 RT at a common site.

This invention includes the specific DNA ligands to HIV-1 RT shown in FIG. 3 (SEQ ID NOS: 6-42), identified by the method described in Example 1. This invention also includes the specific DNA ligands to HIV-1 RT shown in FIG. 4 (SEQ ID NOS: 43–72), as identified by the method described in Example 1. This invention further includes ssDNA ligands of HIV-1 RT that are inhibitors of HIV-1 RT. The scope of the ligands covered by this invention extends to all DNA ligands of HIV-1 RT, modified and unmodified, identified according to the SELEX procedure. More specifically, this invention includes nucleic acid sequences that are substantially homologous to the DNA ligands shown in FIGS. 3 and 4. By substantially homologous it is meant a degree of primary sequence homology in excess of 70%, most preferably in excess of 80%. A review of the sequence homologies of the DNA ligands of HIV-1 RT shown in FIGS. 3 and 4 shows that sequences with little or no primary homology may have substantially the same ability to bind HIV-1 RT. For these reasons, this invention also includes DNA ligands that have substantially the same three-dimensional structure as the ligands presented herein and substantially the same ability to bind HIV-1 RT as the nucleic acid ligands shown in FIGS. 3 and 4. Substantially the same ability to bind HIV-1 RT means that the affinity is within one to two orders of magnitude of the affinity of the ligands described herein. It is well within the skill of those of ordinary skill in the art to determine whether a given sequence—substantially homologous to those specifically described herein—has substantially the same ability to bind HIV-1 RT.

This invention also includes the ligands as described above, wherein certain chemical modifications are made in order to increase the in vivo stability of the ligand or to enhance or mediate the delivery of the ligand. Modifications include chemical substitutions at the deoxyribose and/or phosphate and/or base positions of a given DNA sequence. For example, modifications at the 2' position of the sugar (e.g., replacement of a H at the 2' position with a chloro, fluoro, or O-methyl) may provide resistance to intracellular or extracellular endonucleases. Additionally, a 3' cap consisting of three nucleotides that are connected with phosphodithioate bonds could provide resistance for DNA ligands against 3'–5' exonucleases. Such modifications may be made post-SELEX (modification of previously identified unmodified ligands) or by incorporation into the SELEX process.

The DNA ligands to the HIV-1 RT protein described herein are useful as pharmaceuticals and as part of gene therapy treatments. According to methods known to those skilled in the art, the nucleic acid ligands may be introduced intracellularly into cells infected with the HIV virus, where the nucleic acid ligand will compete with the substrate for the nucleic acid binding site and/or polymerase active site. As such, transcription of HIV genes can be prevented.

The invention also includes the ligands as described above, wherein nucleotide analogs are incorporated at a specific position, and further that these nucleotide analogs possess a reactive group which is able to covalently crosslink the ligand to HIV-1 RT upon binding. This invention also includes the ligands as described above, wherein covalent crosslinking is coupled to the activity of the HIV-1 RT.

The following examples are provided to explain and illustrate the present invention and are not to be taken as limiting of the invention. Example 1 describes the experimental procedures used to generate high-affinity ssDNA ligands to HIV-1 RT. Example 2 describes the high-affinity DNA ligands to HIV-1 RT shown in FIGS. 3 and 4. Example 3 describes suicide inhibitors of HIV-1 RT. Example 4 describes the essential elements of RT1. Example 5 describes the competition between RT1 and RNA Pseudoknot for RT binding.

EXAMPLE 1. EXPERIMENTAL PROCEDURES

Materials. Recombinant HIV-1 RT overexpressed in *E. coli* cells was purified according to the procedure described in Davies, J. F. et al. (1991) Science 252:88–95. Enzyme was aliquoted and stored at −70° C. in HRT Buffer (200 mM KOAc, 50 mM Tris-Acetate, pH 7.4, 6 mM $MgCl_2$, 10 mM DTT). Aliquots thawed and refrozen more than once were discarded. All other materials were purchased from commercial sources.

Generation of Degenerate ssDNA Library. A population of synthetic DNA oligonucleotides (oligo 1) (SEQ ID NO: 1) containing 35 random nucleotides flanked by invariant primer annealing sites was amplified by the Polymerase Chain Reaction (PCR) using oligos 2 (SEQ ID NO: 2) and 3 (SEQ ID NO: 3) as primers (FIG. 1). Oligo 3 (SEQ ID NO: 3) had three biotin phosphoramidites covalently attached to its 5' terminus during synthesis. The 81 nucleotide double-stranded PCR product was size-purified on a 12% non-denaturing acrylamide gel and 100–300 pmol were applied to 100 μl of a Pierce streptavidin-agarose bead matrix suspended in Buffer A (50 mM NaCl, 10 mM Tris-HCl, pH 7.5, 1 mM EDTA). After equilibration for 30 minutes at 20° C. to allow the biotinylated double-stranded DNA (dsDNA) to bind the streptavidin beads, unbound dsDNA was removed with five 500 μl washes of Buffer A, and the matrix-bound dsDNA was denatured in 400 μl of 0.15N NaOH for 15 minutes at 37° C. As these conditions were not harsh enough to disrupt the biotin-streptavidin interaction, denaturation released only the non-biotinylated DNA strand from the bead complex. The free DNA was collected and precipitated, yielding 70–200 pmol of single-stranded DNA (ssDNA). 10–20 pmol were $^{32}p$ labeled at the 5' end with T4 Polynucleotide Kinase and the product was size-purified on an 8% denaturing acrylamide gel and combined with the remaining (unlabeled) ssDNA to comprise the degenerate ssDNA library used for the selections.

Nitrocellulose Filter Binding Assays. Oligonucleotides bound to proteins can be effectively separated from the unbound species by filtration through nitrocellulose membrane filters (Yarus, M. and Berg, P. (1970) Anal. Biochem. 35:450–465; Lowary, P. T. and Uhlenbeck, O. C. (1987) Nucleic Acids Res. 15:10483–10493; Tuerk, C. and Gold, L. (1990) Science 249:505–510). The affinity of the random ssDNA library for HIV-1 RT was determined using a protein excess nitrocellulose filter binding assay as described in Carey, J. et al. (1983) Biochemistry 22:2601–2609. Selections were performed with a saturating ssDNA concentration to promote competition among DNA ligands for a limited number of available target binding sites. The percent of target-dependent DNA retention was minimized for each selection to ensure maximum enrichment of the library for target binders; however, to avoid propagation of members with high affinity for nitrocellulose, selections were repeated if target-free (background) retention was greater than 10% of target-dependent retention.

For the first selection, 500 nM HIV-1 RT and 2 μM ssDNA (100 pmol or about $10^{14}$ different molecules) were equilibrated at 37° C. for 5 minutes in HRT Buffer and filtered through nitrocellulose to sequester target-bound ligands. Target-free selections were done in duplicate to measure and correct for background binding levels. The fraction of total DNA retained by the filters was calculated by measuring radiation without fluor in a scintillation counter. Ligands were harvested from the filter as described in Tuerk, C. and Gold, L. (1990) Science 249:505–510, amplified by PCR, denatured from the biotinylated complementary strand, and end-labeled as described above to regenerate the library. The affinity of the pool for HIV-1 RT was measured prior to selections 6, 8, 10 and 12, and was estimated for the remaining selections. These values determined the ligand concentration necessary for saturation each selection. As the affinity of the population for HIV-1 RT increased, the concentrations of ligand and RT were reduced accordingly to increase selection stringency.

Equilibrium Dissociation Constants. In the simplest case, equilibrium binding of ssDNA ligand (L) to HIV-1 RT protein (P) can be described by equation (1):

$$PL \rightleftharpoons P_f + L_f \quad (1)$$

where $K_d=([P_f][L_f]/[PL])$ is the equilibrium dissociation constant between the protein and ssDNA ligand, $P_f$ is free protein, $L_f$ is free ligand, and PL is protein-ligand complex. Using the mass balance equations, the fraction of bound ligand at equilibrium (q) can be expressed in terms of measurable quantities according to equation (2):

$$q=(P_t+L_t+K_d-((P_t+L_t+K_d)^2-4P_tL_t)^{1/2}) \quad (2)$$

where $P_t$ and $L_t$ are total protein and ligand concentrations.

For competition experiments an additional equilibrium exists between the protein (P) and competitor (C) as described by equation (3):

$$PC \rightleftharpoons P_f + C_f \quad (3)$$

where $K_c=([P_f][C_f]/[PC])$ is the equilibrium dissociation constant between the protein and competitor, $P_f$ is free protein, $C_f$ is free competitor, and PC is protein-competitor complex. Competition titration experiments were analyzed using equation (4) to determine the concentration of free protein as a function of the total competitor concentration:

$$[P_t]=[P_f](1+K_d[L_t]/(1+K_d[P_f])+K_c[C_t]/(1+K_c[P_f])) \quad (4)$$

This equation assumes a 1:1 binding stoichiometry for both reactions and that only one species is bound to protein at a time. Since it is difficult to obtain a direct solution for this equation in terms of $[P_f]$, we have utilized iteration to determine values of $[P_f]$ to a precision of $1\times10^{-15}$. To utilize this equation to follow [PL] as a function of competitor added, we also need the following expression:

$$[PL]=K_d[P_f]([L_t]/(1+K_d[P_f])) \quad (5)$$

These equations were used in the non-linear least-squares data analysis to obtain the best fit parameters for $K_c$ as a function of $[C_t]$ for each competition experiment. The value used for $K_d$ for this fitting analysis was the mean experimental value determined with equation (2) in the absence of competitor.

Inhibition titration experiments were also analyzed using equations (4) and (5), with the primer:template junction substrate as the ligand (L) and the ssDNA ligand the competitor (C). Inhibition values are reported as $K_c'$ rather than $K_i$ (traditionally measured using a Michaelis-Menten analysis comparing reaction rates as a function of substrate concentration) because their mode of inhibition is likely a binding competition between substrate and ssDNA ligand, more accurately described by a $K_c$ value as illustrated above.

Cloning and Sequencing Isolates. Following round 15, one pmol of the library was amplified by PCR using oligo 3 (SEQ ID NO: 3) without the biotins (containing a Pst I restriction endonuclease cleavage site) and oligo 4 (SEQ ID NO: 4) (containing a Bam HI site) as primers (see FIG. 1). Double-stranded products were digested with Pst I and Bam HI and subsequently ligated into pUC19, similarly digested prior to the ligation. The vectors were electroporated into E. coli DH1α cells and oligo 5 (SEQ ID NO: 5), complementary to 16 nucleotides of the PUC19 polylinker region, was used as a primer for dideoxy sequencing of the cloned inserts. These techniques are well-known in the art. A detailed description of these techniques can be found in Schneider, D. et al. (1993) FASEB 7:201–207. Large quantities of individual DNA ligands were prepared by amplifying the vector inserts by PCR using oligos 2 (SEQ ID NO: 2) and 3 (SEQ ID NO: 3) as primers and following the streptavidin matrix purification technique described above to isolate ssDNA.

Assay For Inhibition of RNA-Dependent DNA Polymerase Activity. A substrate for the RNA-dependent DNA polymerase activity of HIV-1 RT was assembled by annealing an 18 nucleotide, 5' end-labeled DNA primer to a 30 nucleotide RNA template with a complementary 3' end (see FIG. 10), and purifying the duplex on a 12% non-denaturing acrylamide gel. The primer sequence matched the 3' terminal 18 nucleotides of tRNA$^{Lys,3}$, responsible for priming minus-strand DNA synthesis of the HIV-1 genome, and the template sequence paralleled the HIV-1 genomic primer binding site and downstream 12 nucleotides. A dilution series of inhibitory ssDNA ligand (to give a final concentration of 0, 1, 3, 9, 27, or 81 nM) was denatured in HRT Buffer at 70° C. for 5 minutes and allowed to renature slowly at 20° C. The primer:template substrate was added to a final concentration of 40 nM, along with dNTP's at 400 μM. The 10 μl reaction was initiated with the addition of either HIV-1, AMV, or MMLV-RT (to give a final concentration of 10 nM), allowed to proceed for 5 minutes at 37° C., and terminated with one volume of formamide. Extension products were separated on an 8% denaturing acrylamide gel and quantitated with an Ambis radioanalytic imager.

Intramolecular Extension Assay. In a 10 μl reaction, 0.1 pmol of 5' end-labeled ssDNA ligand was denatured and slowly renatured as above and combined with 400 μM dNTP's and a saturating concentration of enzyme (200 nM HIV-1 RT, 100 nM AMV RT, or 0.6 units/ml Sequenase T7 DNA polymerase, all shown to have equivalent activity), extended for 30 minutes at 37° C., and terminated with one volume of formamide. To determine the precise location of the annealed 3' end, extensions were also done with Sequenase in the presence of 25 μM ddATP. Extension products were separated on an 8% denaturing acrylamide gel.

Biased Randomization Selections. A library of ligand RT1 variants was chemically synthesized, incorporating the "wild-type" nucleotide at a frequency of 0.625 and each of the "mutant" nucleotides at a frequency of 0.125 in the 35N cassette. Selections for HIV-1 RT affinity were performed as described above; however, a simpler protocol was used to isolate and label the non-biotinylated DNA strand. During the amplification step, α-$^{32}$P dATP was incorporated into both strands of the duplex. The strands were separated on an 8% denaturing acrylamide gel by virtue of the retarded migration of the strand possessing the three biotins, and the non-biotinylated strand was recovered. Because the ssDNA was internally-labeled, end-labeling was not necessary and the recovered sample was ready for the next selection round.

EXAMPLE 2. DNA LIGANDS TO HIV-1 RT

Selected ssDNA Ligands Bind 700 Times Better After 15 SELEX Cycles. Following the selection guidelines described in Example 1, we were able to enrich the DNA library for RT binders from an initial apparent $K_d$ value of 1400 nM to a final value of 4 nM in 12 cycles (see FIG. 2). Enrichment began slowly, requiring 8 cycles to improve the affinity by one log (the apparent $K_d$ of the round 8 library was 150 nM), but increased quickly in the later cycles as predicted by Irvine, D. et al. (1991) J. Mol. Biol. 222:739–761, with the affinity improving another 10-fold by round 10 ($K_d$ equal to 10 nM), and an additional 3-fold by round 12 ($K_d$ equal to 4 nM).

Forty different individuals were isolated after 12 cycles (FIG. 3) (SEQ ID NOS: 6–42). Of the 40 different individuals isolated after 12 cycles, 3 of every 4 contained the pentamer CCCCT (or a variation of this pentamer) in the central 35 nucleotide cassette (FIG. 3). The sequence of the invariant 3' end of each molecule in the library was AGGGG, and when paired to the internal CCCCT, the resulting duplex mimicked a primer:template junction substrate recognized naturally by the enzyme. A more careful analysis revealed additional base pairing: 13 of the 40 paired at least 6 nucleotides, 9 paired at least 7, 3 paired at least 8, and 1 contained the sequence CCCCTGTAG pairing with the 3' terminal CTGCAGGGG at 9 positions. If we assembled a collection of 40 randomly-chosen individuals from the degenerate library, the expected distribution of individuals able to form a duplex with the 3' terminus would be: 20 pairing 5 nucleotides, 4 pairing 6, 2 pairing 7, 1 pairing 8, and 0 pairing 9 (see infra). This overrepresentation of junctions in the degenerate library suggested additional components were required for high affinity binding.

Figure 2:
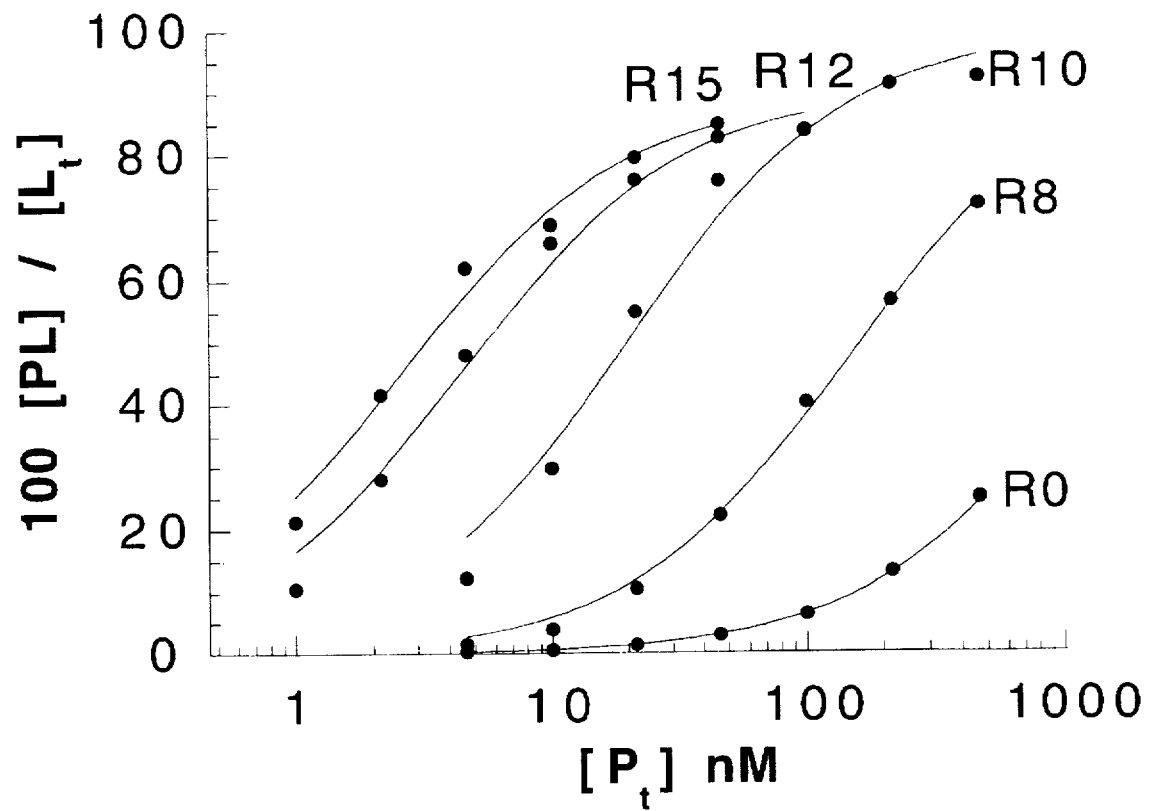
FIG. 2 shows protein excess binding curves measuring affinity of ssDNA library after various SELEX cycles. $K_d$ values were determined using an algorithm to fit the data points to Equation 2 of Example 1.
Figures 5D, 5F:
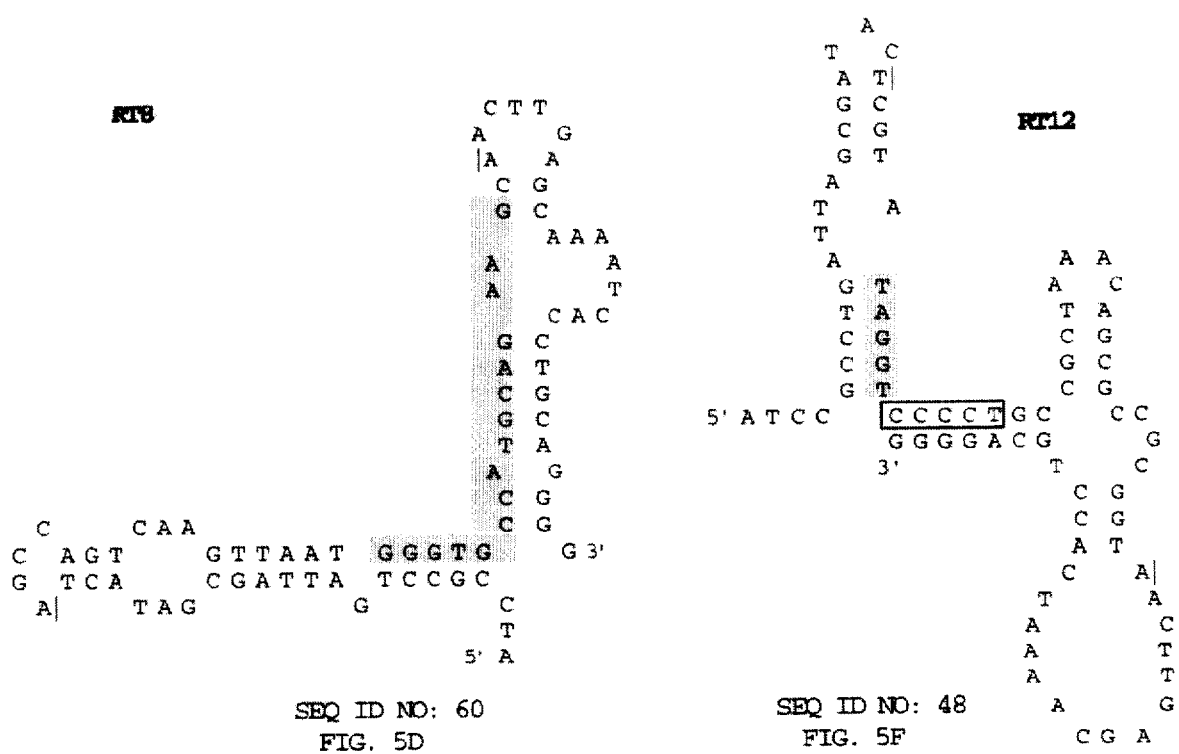
Figure 5G:
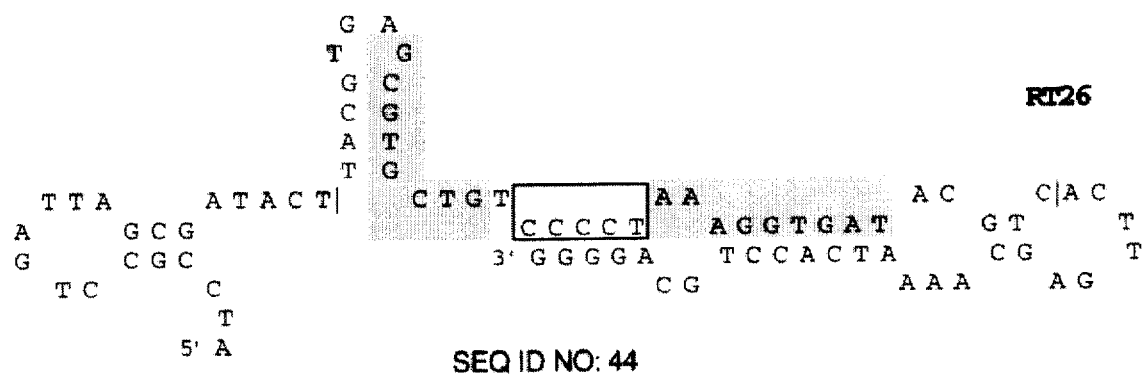
Figure 5H:
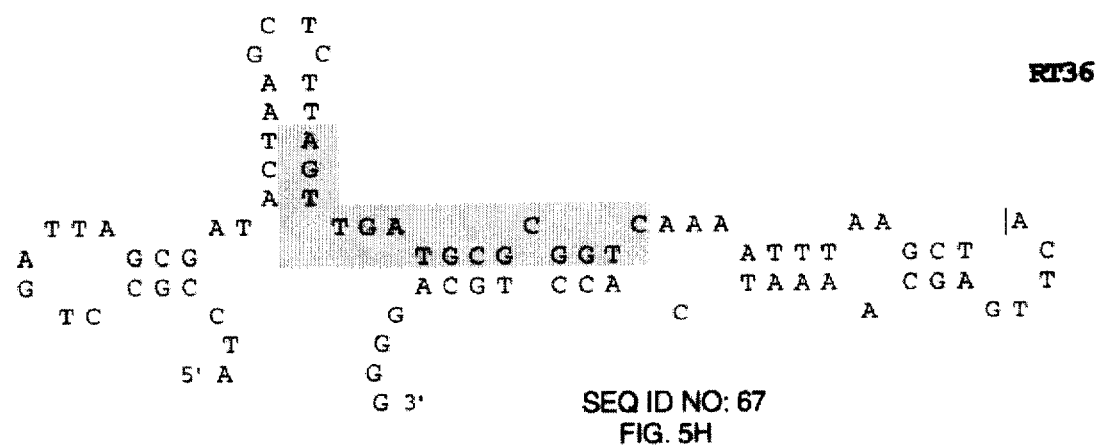

Our decision to isolate and sequence individual members of the enriched library after 12 SELEX cycles was made based on the enrichment profile shown in FIG. 2, where the small affinity change seen between selections ten and twelve suggested sufficient enrichment had occurred. Upon examination of the sequences, two observations were made that led us to believe that further rounds were necessary. First, of the 37 individuals isolated from the enriched library, only three were represented more than once, and none was represented more than two times. Sequence redundancy is often an indicator of sufficient enrichment, as highly represented sequences are believed to possess a component conferring a selectable advantage, ultimately resulting in their enrichment to a significant fraction of the selected library. Second, the majority of molecules selected by HIV-1 RT had the potential to form structures mimicking primer:template junctions. At first, the preference for junctions was discouraging as we hoped to identify ligands with complex, interesting secondary structures, but an analysis of sequence representation (discussed infra) suggested that complex ligands did exist in the degenerate library and might be found with a few more selection cycles.

While most of the selected ligands had the potential to form a primer:template junction, the sequences forming the duplex varied widely among individuals, most often forming imperfect helices with no apparent similarities. Because the frequency of individuals in the degenerate library with this characteristic was very high, specific binding to HIV-1 RT had to depend on more than the presence of a junction. If we accept G:T annealing as a stable base-pair, one of every 2 molecules in the degenerate library possessed a 5 base-pair junction. (This number was derived by calculating the fraction of pentamers with the sequence C/T-C/T-C/T-C/T-T, 1 in 64, multiplying by 31 to account for the number of windows a 35N region provides for a pentamer.) Similar calculations reveal that 1 in 630 individuals in the degenerate library could form a 10 base-pair junction, 1 in $4 \times 10^5$ a 15 base-pair junction, and 1 in $2.7 \times 10^8$ a 20 base-pair junction. The distribution of junction lengths of the round 12 library was unimpressive knowing that approximately 70% of the degenerate library consisted of ligands containing perfect junctions 5 base-pairs long or greater. Clearly, more complex ligands with higher affinity existed in the degenerate library, but were severely outnumbered by the remarkably high representation of individuals (with reasonable affinity for HIV-1 RT) containing a primer:template junction. The tremendous competition for available target binding sites increased the number of cycles necessary to enrich the higher affinity individuals to a sufficient fraction of the population, as predicted by Irvine, D.C., Tuerk, C., and Gold, L. (1991) J. Mol. Bio. 222:739–76.

We performed three more cycles to enrich for molecules possessing binding features in addition to (or instead of) the stable primer:template junction. Individuals isolated from this round 15 library are herein referred to as RT "N," where "N" represents the ligand number corresponding to the sequences shown in FIG. 4 (SEQ ID NOS: 43–72). Only after three additional SELEX cycles did the underrepresented, but structurally more complex individuals surpass those lower affinity members possessing junctions. The majority of individuals in the round 15 library were unable to form primer:template junctions with the 3' terminus, but did have the potential to form ordered structures, primarily long helices with specific interruptions. Individuals able to form junctions that survived the three extra cycles each had additional components that increased their affinity relative to the round 12 library. Of the 30 different individuals isolated from the final population, only 1 of every 3 mimicked a primer:template junction, and those that did shared additional regions of similarity; for example, one subset had in common the octamer GCGTGCTG immediately upstream, and the nonomer AAAGGTGAT immediately downstream of the CCCCT pentamer (FIG. 4). Replacement of the conserved upstream octamer with (dA)8 resulted in a ligand with an affinity for HIV-1 RT as poor as the degenerate library (data not shown).

Compared with the isolates of the round 12 library, more members of the round 15 library were multiply represented (RT6 (SEQ ID NO: 57) was represented 7 times, RT8 (SEQ ID NO: 60) 4 times, RT12 (SEQ ID NO: 48) 3 times, etc.), indicating a more highly enriched representation of HIV-1 RT binders existed after 15 cycles. The high number of redundant sequences and conserved elements in the round 15 library indicated that further enrichment was unnecessary. The three additional cycles resulted in a decrease in the apparent $K_d$ of the library to 2 nM, a total increase in affinity of 700-fold over the degenerate library. The isolates from this library were classified into subsets with common sequence elements. At least one from each subset (for a total of 8) was chosen for further characterization.

HIV-1 RT Binders Characterized by Long Interrupted Helices. The primary sequence diversity between subsets suggested that if there was a common element responsible for the affinity, it existed at a higher level of structure. Unfortunately, a reliable set of rules characterizing the folding of ssDNA molecules has not been elucidated, restricting us to use of the best tool available, an algorithm that uses rules for RNA folding to predict secondary structure (Jaeger, J. A. et al. (1989) Proc. Natl. Acad. Sci., U.S.A. 86:7706–7710; Zuker, M. (1989) Science 244:48–52).

Potential structures offered by this algorithm for each of the eight ssDNA ligands are illustrated in FIGS. 5A–H. Optimal and suboptimal structures were compared within each group, and conserved structural elements were used to predict functional binding motifs. All of the ligands have the potential to form structures characterized by a high degree of base pairing, often making extensive use of the invariant regions to form long helices interrupted by mismatches, bulges, and internal loops. Ligands RT10 (SEQ ID NO: 56), RT12 (SEQ ID NO: 48), and RT26 (SEQ ID NO: 44) are able to pair their 3' terminal AGGGG with an internal CCCCT to form an intramolecular primer:template junction. Of particular interest is the helix of RT26 (SEQ ID NO: 44), containing a potential internal loop with an AA opposite a CG as shown in FIG. 6A. This motif can also be formed in ligand RT1 (SEQ ID NO: 71), as well as variants in ligands RT4 (SEQ ID NO: 64) (an AA opposite an AG), RT8 (SEQ ID NO: 60) (a CAA opposite a TAG), and RT36 (SEQ ID NO: 67) (an AA opposite an A) (FIGS. 6B–E).

Figure 7A:
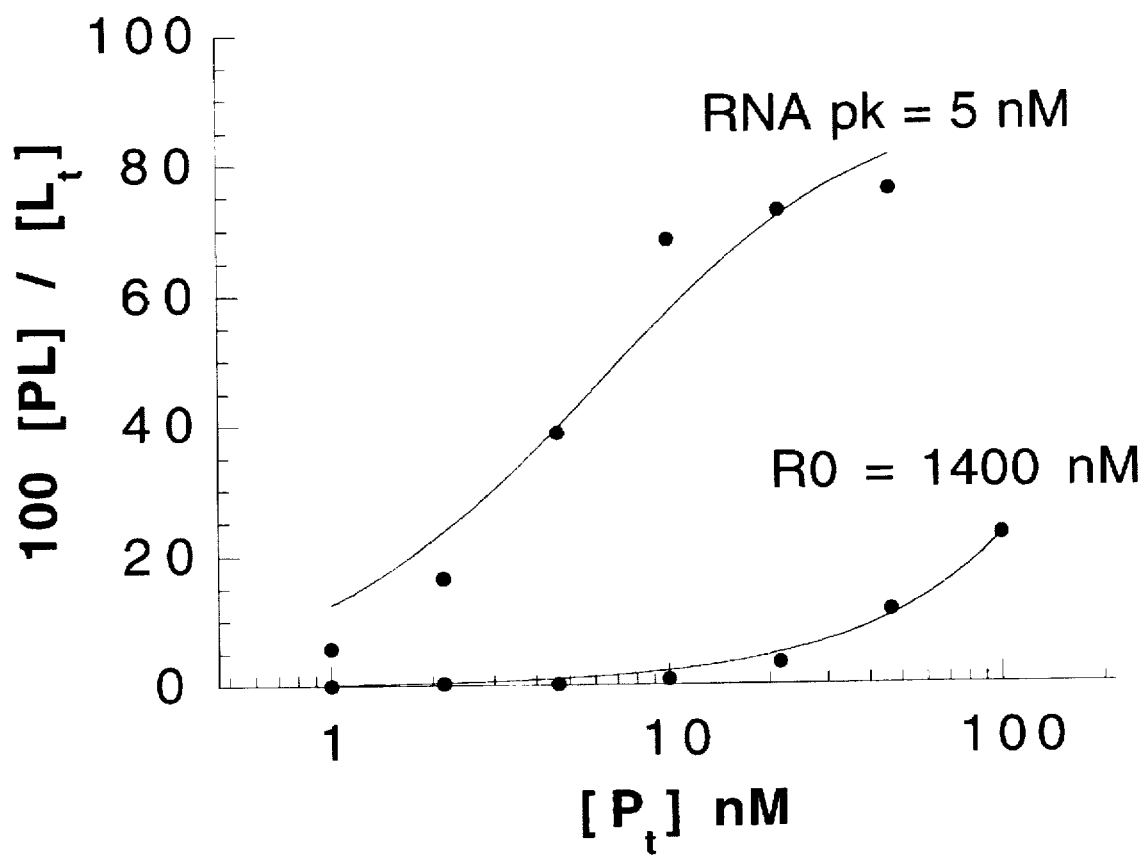
FIGS. 7A–7C show the protein excess binding curves of selected individuals. The percent of ligand bound is plotted as a function of total protein concentration. The dissociation constants of the RNA pseudoknot (RNA pk) and the degenerate library (R0) are shown in FIG. 7A. The dissociation constants of RT1 (SEQ ID NO: 71), RT4 (SEQ ID NO: 64), RT6 (SEQ ID NO: 57), RT8 (SEQ ID NO: 60), RT10 (SEQ ID NO: 56), RT12 (SEQ ID NO: 48), RT26 (SEQ ID NO: 44), and RT36 (SEQ ID NO: 67) are shown in FIGS. 7B and 7C. Dissociation constants were determined as in Example 1.
Figure 7B:
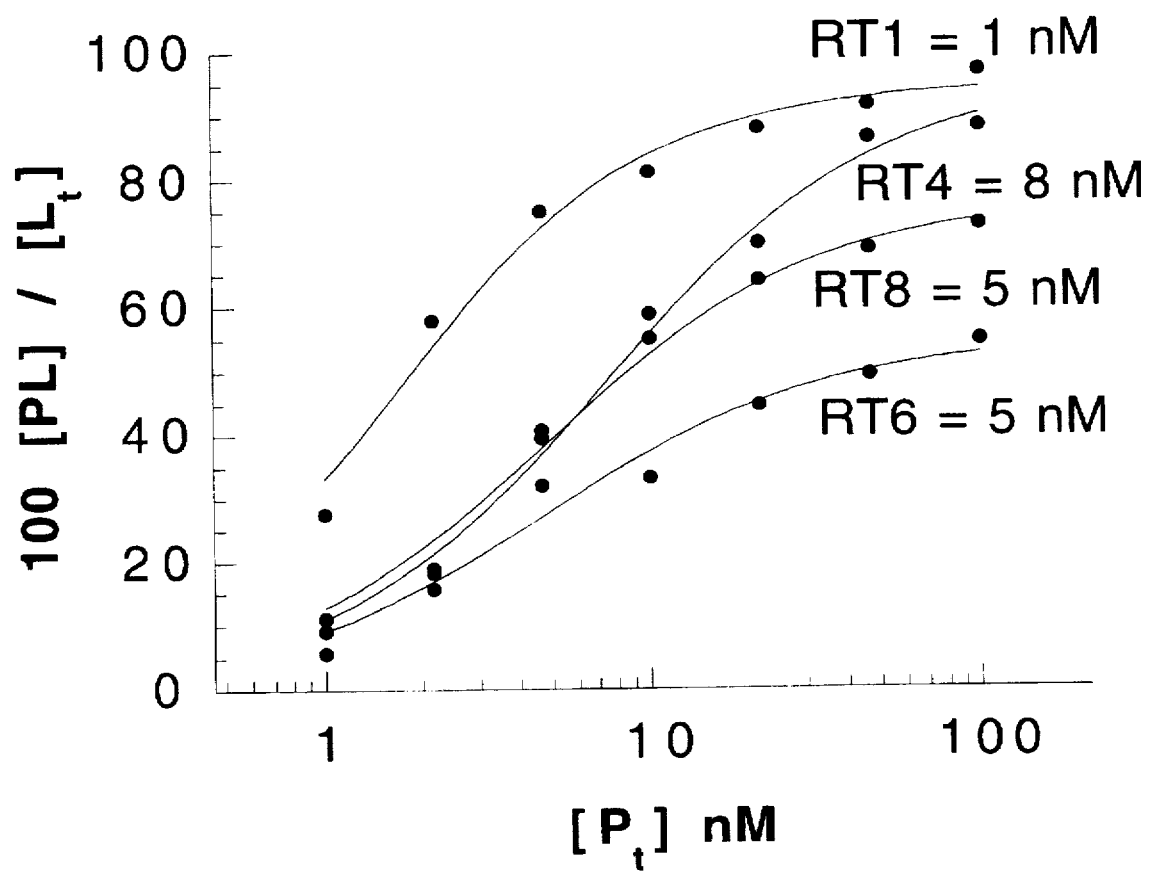
Figure 7C:
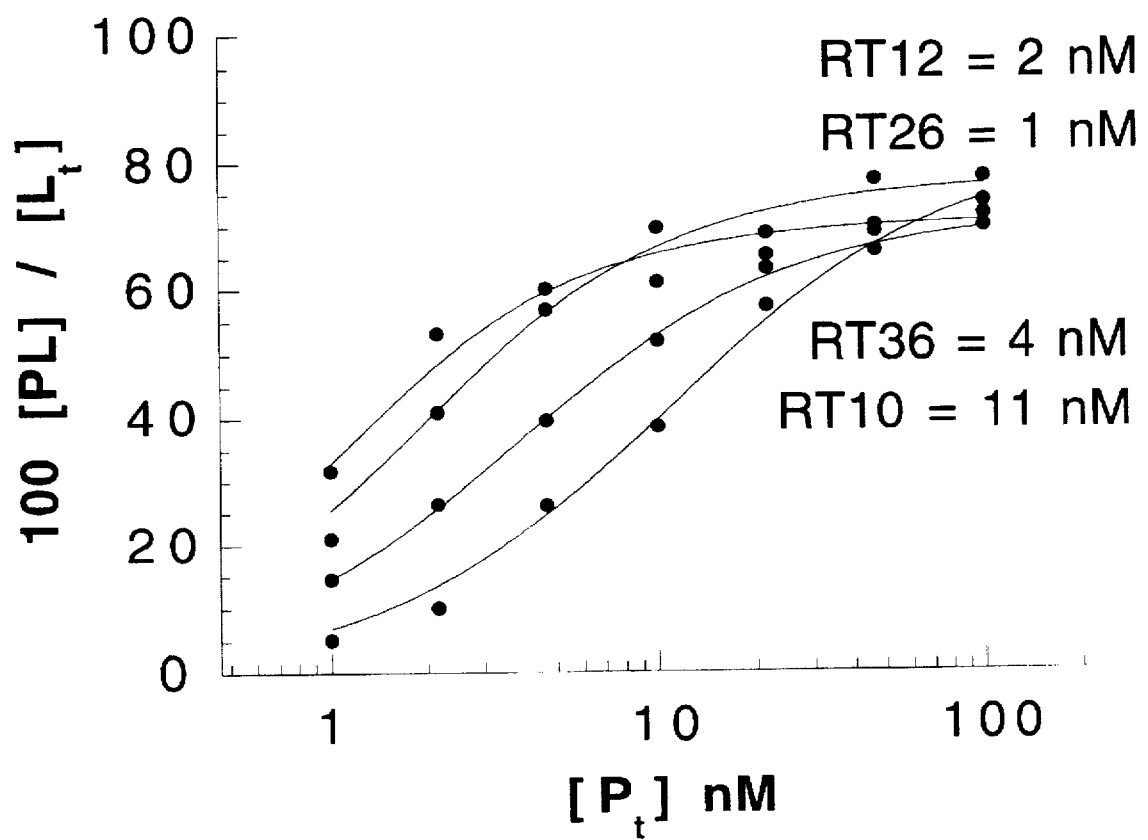
Figure 8:
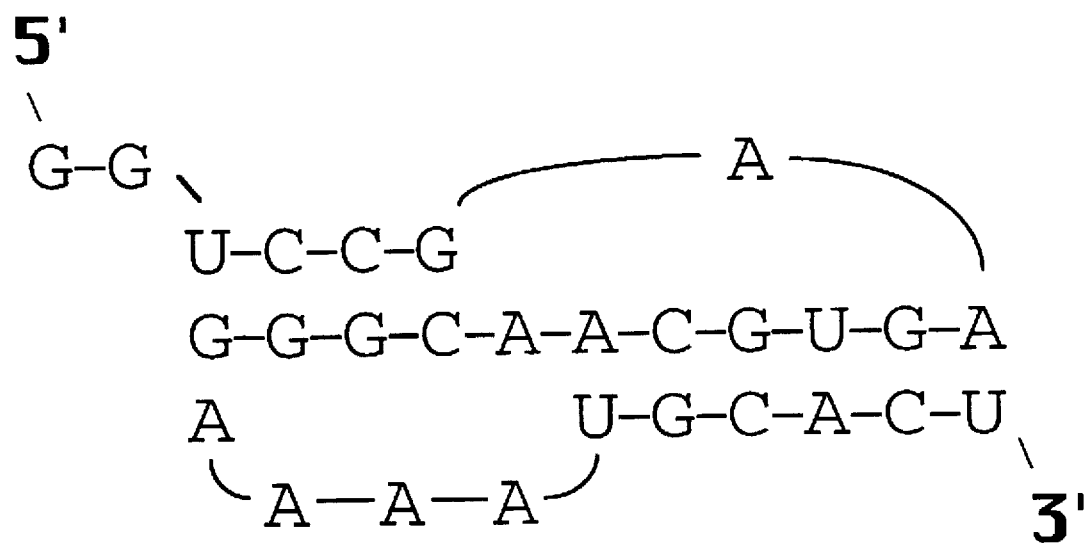
FIG. 8 shows the proposed secondary structure of the RNA pseudoknot inhibitor (SEQ ID NO: 73) (Tuerk, C. et al. (1992) Proc. Natl. Acad. Sci. U.S.A. 89:6988–6992).

Binding Curves Confirm High Affinity of Individual Ligands. Affinity values of each of the eight chosen isolates for HIV-1 RT were measured using the filter binding assay described in Example 1 (FIGS. 7A–C). The RNA pseudoknot inhibitor reported in Tuerk, C. et al. (1992) Proc. Natl. Acad. Sci., U.S.A. 89:6988–6992 and U.S. patent application No. 07/964,624 now issued as U.S. Pat. No. 5,496,938, (see FIG. 8) had an affinity of 5 nM under our conditions, while that of the degenerate library (RO) is 1400 nM. Isolates RT1 (SEQ ID NO: 71) and RT26 (SEQ ID NO: 44) exhibited the highest affinity having a $K_d$ value of approximately 1 nM, while the others ranged from 2 to 11 nM. Differences in maximum percent bound likely reflect competing ligand structures with lower affinity. No correlation exists between representation in the fully-enriched library (see FIG. 4) and affinity for HIV-1 RT, as ligand RT1 (SEQ ID NO: 71) ($K_d$=1 nM), represented once, has a higher affinity than RT6 (SEQ ID NO: 57) ($K_d$=5 nM), represented 7 times. Indicated dissociation constants were determined as in Example 1. No significant correlation was observed between the affinity of a molecule and the subset into which it was classified in FIG. 4, as the three highest affinity ligands (RT1 (SEQ ID NO: 71), RT12 (SEQ ID NO: 48), and RT26 (SEQ ID NO: 44) were each classified into different subsets. However, both RT1 (SEQ ID NO: 71) and RT26 (SEQ ID NO: 44) contain the internal loop structure shown in FIGS. 6A and B, suggesting a possible participation of this motif in conferring high affinity upon ligands that possess it.

Figure 9:
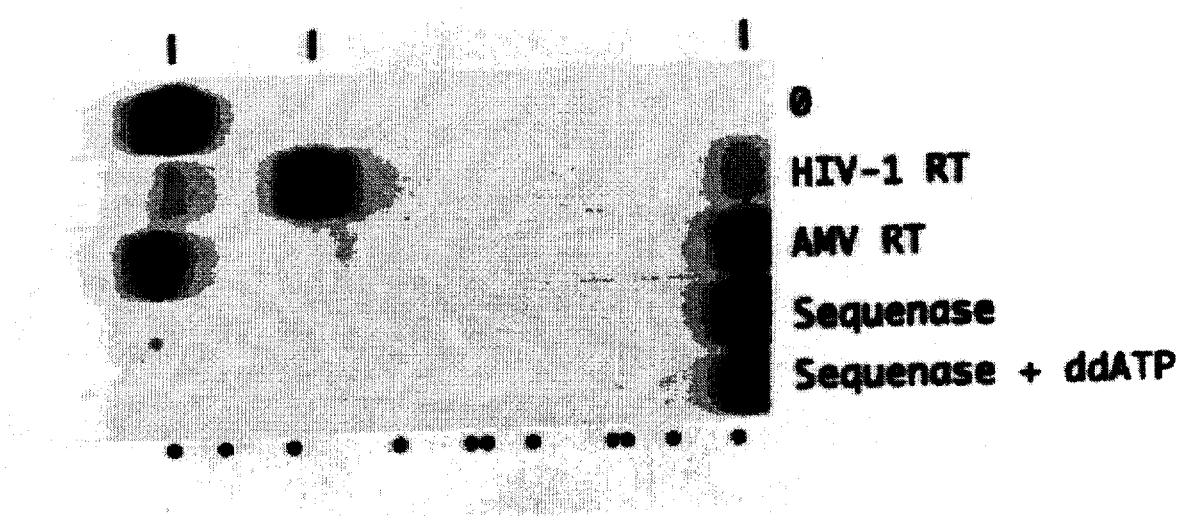
FIG. 9 shows the products of intramolecular extension of RT26 (SEQ ID NO: 44). End-labeled RT26 was extended with a saturating concentration of either HIV-1 RT, AMV RT, or Sequenase.
Figure 13:
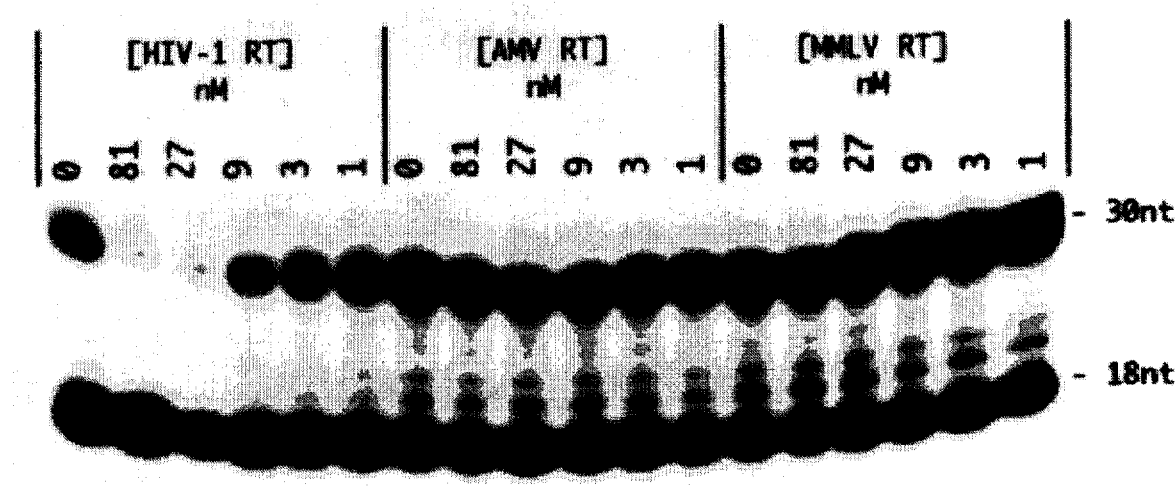
FIG. 13 shows the inhibition specificity assay. Inhibition of the RNA-dependent DNA polymerase activity of three reverse transcriptases (HIV-1 RT, AMV RT, and MMLV RT) was performed as described in Example 1, with inhibitor RT1t49 (SEQ ID NO: 73) present at the indicated concentrations in nM.
Figure 14:
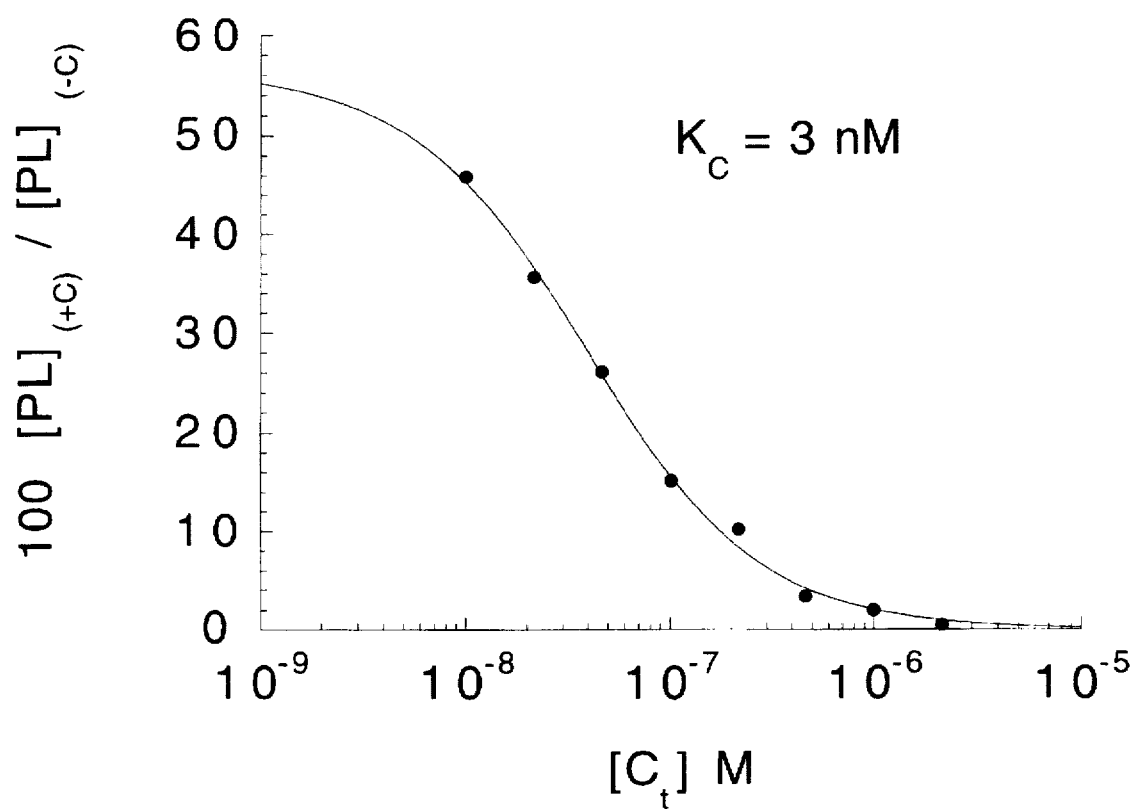
FIG. 14 shows the competitive binding of RT1 (SEQ ID NO: 71) and the RNA pseudoknot (RNA pk) (SEQ ID NO: 73).

Intramolecular Extension Verifies Secondary Structure Predictions. The isolates possessing an intramolecular primer:template junction (RT10 (SEQ ID NO: 56), RT12 (SEQ ID NO: 48), and RT26 (SEQ ID NO: 44)) were assayed for the ability to be extended from their 3' termini by a variety of polymerases. The results for RT26 are shown in FIG. 9. When extended with a saturating concentration of HIV-1 RT, initiation was nearly 100%, while extension proceeded only 5–8 nucleotides before premature termination occurred. AMV-RT initiated only 50%, but extension proceeded to the end of the template. With Sequenase T7 DNA polymerase, both initiation and extension went to completion. The sequence pattern created by extending with Sequenase in the presence of ddATP confirmed the proposed annealing site of the 3' end of RT26 (SEQ ID NO: 44). This was also true for RT10 (SEQ ID NO: 56) and RT12 (SEQ ID NO: 48) (data not shown).

The premature terminations seen when extending RT26 with HIV-1 RT appear to be specific for that enzyme. Both products (premature and complete) were isolated and found to have 100-fold lower affinity for HIV-1 RT than the unextended RT26 (SEQ ID NO: 44) (data not shown). HIV-1 RT is less processive than AMV RT and Sequenase, and this lack of processivity might explain the premature termination, although using a saturating concentration of enzyme should have reduced this effect. Two alternative explanations for the premature termination are that addition of the 5–8 templated nucleotides to the 3' end of RT26 (SEQ ID NO: 44) creates a low-affinity product, resulting in the release of enzyme more frequently than addition of the next nucleotide, or a trapped product unable to release enzyme or be further extended. Premature termination of RT26 (SEQ ID NO: 44) extension occurred within the stem of a potential hairpin, suggesting termination was simply a result of interference by secondary structure; however, similar premature terminations occurred with RT10 (SEQ ID NO: 56) and RT12 (SEQ ID NO: 48) (data not shown), neither of which occurred at positions stabilized by secondary structure.

A groove on the surface of HIV-1 RT, shown by the X-ray structure to extend from the polymerase catalytic site to the RNase H active site (Kohlstaedt, L. A. et al. (1992) Science 256:1783–1790; Jacobo-Molina, A. et al. (1993) Proc. Natl. Acad. Sci., U.S.A. 90:6320–6324; Arnold, E. et al. (1992) Nature 357:85–89; Krug, M. S. and Berger, S. L. (1991) Biochemistry 30:10614–10623), is the best candidate for the protein region contacted by the selected DNA ligands. The ability of RT10 (SEQ ID NO: 56) and RT12 (SEQ ID NO: 48), and RT26 (SEQ ID NO: 44) to be extended demands that the 3' end of these ligands be present in the polymerase active site when they are bound, likely positioned there by interactions between the helix and the protein groove.

Inhibition of Polymerase Activity Suggests Interaction at Substrate Binding Site and/or Active Site. The ability of each of the 8 isolates to inhibit the RNA-dependent DNA polymerase activity of HIV-1 RT was assayed by measuring the decrease in extension product formation from a primer::template substrate as a function of inhibitor concentration (FIGS. 10A–10E). The substrate for the inhibition assay was a DNA:RNA heteroduplex consisting of an 18 nucleotide end-labeled DNA primer (SEQ ID NO: 74) identical in sequence to the 3' end of tRNA$^{Lys,3}$ annealed to a 30 nucleotide RNA template (SEQ ID NO: 75) whose sequence matches the genomic primer binding site and the first twelve transcribed nucleotides. Extension reactions were performed as described in Example 1 in the presence of 0, 81, 27, 9, 3, and 1 nM inhibitor as indicated in FIG. 10.

The two bands on the gels are the unextended DNA primer migrating as an 18-mer, and the extended DNA product migrating as a 30-mer. The percent of primer extended as a function of inhibitor concentration is plotted for each inhibitor. $K_i$ values were determined using a least-squares algorithm to fit the data points to Equations 4 and 5 of Example 1. We report these $K_i'$ values rather than true $K_i'$ values because they were not determined with a standard Michaelis-Menten kinetic assay (comparing double-reciprocal plots of reaction velocity as a function of substrate concentration in the presence and absence of inhibitor). However, the correlation between the $K_i'$ and $K_d$ values suggests that the mechanism of inhibition may be a competition between the inhibitory ligand and the substrate for the nucleic acid binding site and/or polymerase active site of RT, although this has not been tested directly.

Almost no inhibition was seen with as high as 81 nM of the degenerate ssDNA library present (RO, $K_i' \leq 3$ μM). The RNA pseudoknot (RNA pk) inhibited the activity of HIV-1 RT with a $K_i'$ value of 4.7 nM under our conditions, consistent with the $K_d$ value shown in FIG. 7 and Tuerk, C. et al. (1992) Proc. Natl. Acad. Sci., U.S.A. 89:6988-6992. The $K_i'$ values of the seven ssDNA ligands assayed (only RT1 (SEQ ID NO: 71) and RT26 (SEQ ID NO: 44) are shown) were also consistent with the $K_d$ values shown in FIGS. 7A-C. Clones RT1 (SEQ ID NO: 74) and RT26 (SEQ ID NO: 44) were the most potent inhibitors of the RNA-dependent DNA polymerase activity of HIV-1 RT, having $K_i'$ values of 0.3 nM and 2.7 nM, respectively. The $K_i'$ values of RT4 (SEQ ID NO: 64), RT6 (SEQ ID NO: 57), RT8 (SEQ ID NO: 60), RT10 (SEQ ID NO: 56), and RT36 (SEQ ID NO: 67) are 4.1 nM, 30 nM, 13 nM, 62 nM, and 6.5 nM, respectively. The $K_i'$ value of RT12 (SEQ ID NO: 48) was not calculated. The correlation between the $K_i'$ and $K_d$ values suggests that the mechanism of inhibition may be a competition between the inhibitory ligand and the substrate for the nucleic acid binding site and/or polymerase active site of RT.

EXAMPLE 3. SUICIDE INHIBITORS OF HIV-1 RT

The specificity and high affinity for HIV-1 RT exhibited by these ssDNA ligands make them good candidates for suicide inhibitors of HIV-1 RT. This is accomplished by synthesizing a particular ssDNA ligand to HIV-1 RT, incorporating at specific positions nucleotide analogs possessing a reactive group able to covalently crosslink the ligand to HIV-1 RT upon binding. This attachment event would render the enzyme permanently non-functional. Reactive groups are chosen to utilize the specificity of the ligands for HIV-1 RT, being reactive only with HIV-1 RT and only when in close proximity (i.e., only when bound). We have shown that HIV-1 can catalyze addition of a nucleotide to the 3' end of RT10 (SEQ ID NO: 56), RT12 (SEQ ID NO: 48), and RT26 (SEQ ID NO: 44). The ability of the existing HIV-1 RT ligand to extend by addition of a nucleotide to the 3'-end can be exploited for mechanism-based suicide inhibition of the enzyme. This will result in covalent linking of the ligand to the target.

The crucial step in addition of a nucleotide onto the 3'-end of the existing ligand is the abstraction of the proton from the 3'-hydroxyl group by a base associated with the enzyme. Proton extraction or activation of the 3'-hydroxyl aids in the attack of the α-phosphorous of the incoming nucleoside triphosphate. A 3'-terminal nucleoside analog can be designed, that exploits base-activation of the 3'-hydroxyl group to form a reactive intermediate. This species, which is generated in close proximity to the enzyme surface, is then ready to accept an enzyme nucleophile to generate a covalent link.

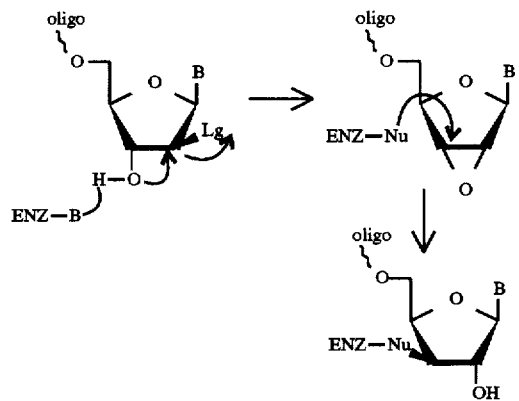

The terminal 3'-nucleotide is modified to bear a leaving group at the 2'-position in anti stereoconfiguration to the 3'-hydroxyl. A typical leaving group could be a halogen, an acetyl group, a sulfonate group, a carbonate group, an acetamide group or any other leaving group. Upon deprotonation of the 3'-hydroxyl by the enzyme a 2',3'-epoxide is formed on the α-face of the nucleoside. This epoxide is labile enough to be attacked from the β-face of the furanose by any adjacent nucleophile on the enzyme. This process results in a covalent link between the enzyme and the ligand.

To increase specificity of inhibition, covalent crosslinking could be coupled to activity of the enzyme. If RT10 (SEQ ID NO: 56), RT12 (SEQ ID NO: 48), and RT26 (SEQ ID NO: 44) were synthesized with a nucleotide analog at its 3' end containing an electron withdrawing group at the 2' carbon, catalytic addition of a nucleotide triphosphate (step 1 of FIG. 15) would result in a spontaneous elimination event, releasing the newly added nucleotide and yielding an electrophilic carbon at the 3' position of the sugar polarized by the electron withdrawing group at the 2' position (step 2 of FIG. 15). The reactive 3' carbon would be available for attack by any good nucleophilic group in the vicinity, resulting in the formation of a covalent crosslink between the protein and the ligand (step 3 of FIG. 15). Because this reaction is dependent on catalysis by HIV-1 RT, these inhibitors would specifically target active enzyme. It is possible that RT10 (SEQ ID NO: 56), RT12 (SEQ ID NO: 48), and RT26 (SEQ. ID NO: 44) interact with HIV-1 RT in such a way that there are two aspartic acid residues and one tyrosine near enough to perform the reaction.

EXAMPLE 4. ESSENTIAL ELEMENTS OF RT1

Biased Synthesis SELEX Identifies Essential Elements of RT1. From a library of RT1 mutants, synthesized as described in Example 1, we selected those maintaining a high affinity for HIV-1 RT. In six SELEX cycles the affinity of the library increased almost 1000-fold, from 1500 nM to approximately 2 nM (data not shown). About one half of the 32 isolates had a primary sequence consistent with the predicted secondary structure of RT1 (SEQ ID NO: 71), while the other half adopted alternative structures with equally high affinity. The sequences of the isolates similar in structure to RT1 are shown in FIG. 11 (SEQ ID NOS: 76-81). The acceptability of mutations varied with position:

mutations in the 3' region of the randomized cassette (positions 29–35) were most tolerated, while those in the 5' region (positions 1–7) eliminated ability to bind HIV-1 RT and were selected against. Conservation of positions 1–3 and 6–9 support the internal loop duplex structure comprising the predicted 5' domain of RT1 when paired with the 5' invariant primer-binding region. Additional support for the base-pairing pattern in this domain is provided by the acceptability of the A to G substitution at position 2, which is able to maintain the base pair with the invariant T. The small hairpin predicted to exist in the central domain of RT1 (SEQ ID NO: 71) is not supported by the results of this experiment. In the stem of the proposed hairpin, many substitutions disrupting the base-pairing pattern were acceptable, and alternative structures were preferred. No predicted structure could accommodate each of the selected individuals, suggesting the absence of secondary structure in this region. HIV-1 RT might recognize specific unpaired residues of this central domain of RT1, possibly those indicated in the consensus illustrated in FIG. 11B (SEQ ID NO: 92).

Only 49 Nucleotides Required of RT1 for High Affinity. Truncated versions of ligand RT1 (SEQ ID NO: 71) were synthesized and predicted secondary structures are shown in FIGS. 12A–12C. The predicted secondary structures, (using the RNA folding algorithm of Zuker, J. A. et al. (1989) Science 244:48–52) were refined by the results of the biased randomization experiment, in particular, the lack of secondary structure in the central region. These truncates were tested for their ability to bind HIV-1 RT with high affinity. RT1t30 (SEQ ID NO: 94), composed of the first 30 nucleotides of RT1 containing the internal loop duplex, showed no significant binding below 1 μM HIV-1 RT. However, addition of the next 19 nucleotides, comprising the central stem and loop motif, produced a 49-mer (RT1t49) (SEQ ID NO: 93) which bound HIV-1 RT with an affinity of 4 nM, nearly as high as the full-length 81 nucleotide RT1. The relative affinities of RT1 (SEQ ID NO: 71), RT1t30 (SEQ ID NO: 94), and RT1t49 (SEQ ID NO: 93) suggest that all of the specific binding components of RT1 (SEQ ID NO: 71) exist in the first 49 nucleotides and that while the internal loop motif is insufficient alone, it likely participates in the interaction with HIV-1 RT in combination with other specific binding components.

49-mer Inhibits HIV-1 RT Specifically. The inhibition assay described in Example 1 was also used to determine the specificity of inhibition of the RNA-dependent DNA polymerase activity of HIV-1 RT. Using ligand RT1t49 (SEQ ID NO: 93) as the competitor, we compared in parallel the ability to inhibit the polymerase activity performed by HIV-1 RT, AMV RT, and MMLV RT. As illustrated in FIG. 13, inhibition of primer extension was seen when performed with HIV-1 RT, but was not detectable when performed with AMV RT and MMLV RT, even at inhibitor concentrations as high as 81 nM. The lack of inhibition of AMV RT and MMLV RT possibly suggests that RT1t49 (SEQ ID NO: 93) may have a lower affinity for these enzymes, requiring higher concentrations of RT1t49 (SEQ ID NO: 93) to see an inhibitory effect on primer extension.

EXAMPLE 5. RT1 Competes With RNA Pseudoknot for RT Binding The specific inhibition characteristics exhibited by both an RNA pseudoknot and a ssDNA ligand posed the question of whether two apparently dissimilar molecules, at least at the level of secondary structure, interact with HIV-1 RT at a common nucleic acid binding site. To test this, we measured the ability of the ssDNA ligand RT1 (SEQ ID NO: 71) to maintain its specific binding contacts with HIV-1 RT in the presence of high concentrations of RNA pseudoknot (see FIG. 8). FIG. 14 shows the competitive binding of RT1 (SEQ ID NO: 71) and the RNA pseudoknot (RNA pk) (SEQ ID NO: 73). The percent of RT1 bound in the presence of competitor relative the percent bound in the absence of competitor is plotted as a function of RNA pk concentration. The $K_c$ value for RNA pk (3 nM) was determined using an algorithm that fit the data points to Equations 4 and 5 in Example 1, and was consistent with the Kd value (5 nM) measured using the nitrocellulose filter binding assay described in Example 1. As shown graphically in FIG. 14, when a stoichiometric equivalent of RNA pk was added, approximately one half of the complexed RT1 was displaced, and nearly all was displaced when a large excess of RNA was added. These results leave little doubt that binding of RT1 (SEQ ID NO: 71) and RNA pk (SEQ ID NO: 73) to HIV-1 RT are mutually exclusive. However, with this assay we are unable to distinguish between an interaction of both ligands at a common site or an interaction of each at different sites, with a conformational change upon binding the first that prevents subsequent binding of the second.

SEQUENCE LISTING ( 1 ) GENERAL INFORMATION:

( i i i ) NUMBER OF SEQUENCES: 94

( 2 ) INFORMATION FOR SEQ ID NO:1:

( i ) SEQUENCE CHARACTERISTICS:
( A ) LENGTH: 81
( B ) TYPE: nucleic acid
( C ) STRANDEDNESS: single
( D ) TOPOLOGY: linear ( x i ) SEQUENCE DESCRIPTION: SEQ ID NO:1:

CCCCTGCAGG TGATTTTGCT CAAGTNNNNN NNNNNNNNNN NNNNNNNNNN 50

NNNNNNNNNN AGTATCGCTA ATCAGGCGGA T 81

( 2 ) INFORMATION FOR SEQ ID NO:2:

( i ) SEQUENCE CHARACTERISTICS:
  ( A ) LENGTH: 21
  ( B ) TYPE: nucleic acid
  ( C ) STRANDEDNESS: single
  ( D ) TOPOLOGY: linear ( x i ) SEQUENCE DESCRIPTION: SEQ ID NO:2:

ATCCGCCTGA TTAGCGATAC T     21

( 2 ) INFORMATION FOR SEQ ID NO:3:

( i ) SEQUENCE CHARACTERISTICS:
  ( A ) LENGTH: 25
  ( B ) TYPE: nucleic acid
  ( C ) STRANDEDNESS: single
  ( D ) TOPOLOGY: linear ( i x ) FEATURE:
  ( A ) NAME/KEY: N
  ( B ) LOCATION: 1
  ( C ) OTHER INFORMATION: This symbol stands for biotintylated cytosine.

( x i ) SEQUENCE DESCRIPTION: SEQ ID NO:3:

NCCCTGCAGG TGATTTTGCT CAAGT     25

( 2 ) INFORMATION FOR SEQ ID NO:4:

( i ) SEQUENCE CHARACTERISTICS:
  ( A ) LENGTH: 49
  ( B ) TYPE: nucleic acid
  ( C ) STRANDEDNESS: single
  ( D ) TOPOLOGY: linear ( x i ) SEQUENCE DESCRIPTION: SEQ ID NO:4:

CCGAAGCTTA ATACGACTCA CTATAGGGAT CCGCCTGATT AGCGATACT     49

( 2 ) INFORMATION FOR SEQ ID NO:5:

( i ) SEQUENCE CHARACTERISTICS:
  ( A ) LENGTH: 16
  ( B ) TYPE: nucleic acid
  ( C ) STRANDEDNESS: single
  ( D ) TOPOLOGY: linear ( x i ) SEQUENCE DESCRIPTION: SEQ ID NO:5:

TTCACACAGG AAACAG     16

( 2 ) INFORMATION FOR SEQ ID NO:6:

( i ) SEQUENCE CHARACTERISTICS:
  ( A ) LENGTH: 81
  ( B ) TYPE: nucleic acid
  ( C ) STRANDEDNESS: single
  ( D ) TOPOLOGY: linear ( x i ) SEQUENCE DESCRIPTION: SEQ ID NO:6:

ATCCGCCTGA TTAGCGATAC TCAGGCTCCT GAGTGAAGTG CGGACATGTA     50

CCNNNNACTT GAGCAAAATC ACCTGCAGGG G     81

( 2 ) INFORMATION FOR SEQ ID NO:7:

( i ) SEQUENCE CHARACTERISTICS:
  ( A ) LENGTH: 81
  ( B ) TYPE: nucleic acid
  ( C ) STRANDEDNESS: single
  ( D ) TOPOLOGY: linear ( x i ) SEQUENCE DESCRIPTION: SEQ ID NO:7:

ATCCGCCTGA TTAGCGATAC TCGCCAGGCC CCTGTAGTCG GGCGGAGTCA    50

NNNNNNACTT GAGCAAAATC ACCTGCAGGG G    81

( 2 ) INFORMATION FOR SEQ ID NO:8:

( i ) SEQUENCE CHARACTERISTICS:
        ( A ) LENGTH: 82
        ( B ) TYPE: nucleic acid
        ( C ) STRANDEDNESS: single
        ( D ) TOPOLOGY: linear ( x i ) SEQUENCE DESCRIPTION: SEQ ID NO:8:

ATCCGCCTGA TTAGCGATAC TCGTATAGGT CCCCTGCCGC TAAACAGCGC    50

CGCGGTAACT TGAGCAAAAT CACCTGCAGG GG    82

( 2 ) INFORMATION FOR SEQ ID NO:9:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:9:

ATCCGCCTGA TTAGCGATAC TCTGCCAGTC CCCTGTAATT AGACGGAAAC    50

TCCTGTACTT GAGCAAAATC ACCTGCAGGG G    81

( 2 ) INFORMATION FOR SEQ ID NO:10:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:10:

ATCCGCCTGA TTAGCGATAC TCAGCAGTCC CCCTATTCAT GGGCCCGCGG    50

TTCATGACTT GAGCAAAATC ACCTGCAGGG G    81

( 2 ) INFORMATION FOR SEQ ID NO:11:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:11:

ATCCGCCTGA TTAGCGATAC TTAACGCCAG GCCCCTGTAA TAGTGCGGAT    50

CGACAGACTT GAGCAAAATC ACCTGCAGGG G    81

( 2 ) INFORMATION FOR SEQ ID NO:12:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:12:

ATCCGCCTGA TTAGCGATAC TGAGCTGTTG TACAGTGCAA GTGTAGCAGT    50

TCCCCTACTT GAGCAAAATC ACCTGCAGGG G    81

( 2 ) INFORMATION FOR SEQ ID NO:13:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
ATCCGCCTGA TTAGCGATAC TGTATCTTTA GTACAAGTGC TCGGCAGCTC        50
CCCCACACTT GAGCAAAATC ACCTGCAGGG G                            81
```

( 2 ) INFORMATION FOR SEQ ID NO:14:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:14:

```
ATCCGCCTGA TTAGCGATAC TTCGCCAGTC CCTGTTTCA GCGCGGATAT         50
GACCATACTT GAGCAAAATC ACCTGCAGGG G                            81
```

( 2 ) INFORMATION FOR SEQ ID NO:15:

( i ) SEQUENCE CHARACTERISTICS:
        ( A ) LENGTH: 80
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
ATCCGCCTGA TTAGCGATAC TGTATGGCTC TCAGCCCAGG CCCCTGATAC        50
AGTCGACTTG AGCAAAATCA CCTGCAGGGG                              80
```

( 2 ) INFORMATION FOR SEQ ID NO:16:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:16:

```
ATCCGCCTGA TTAGCGATAC TGAAGAGCGT GCTGTCCCCT TAGGGTAATT        50
GTCNNNACTT GAGCAAAATC ACCTGCAGGG G                            81
```

( 2 ) INFORMATION FOR SEQ ID NO:17:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:17:

```
ATCCGCCTGA TTAGCGATAC TACGCGTGCT GCCCCATAAC GGTGGCTTCA        50
ANNNNNACTT GAGCAAAATC ACCTGCAGGG G                            81
```

( 2 ) INFORMATION FOR SEQ ID NO:18:

( i ) SEQUENCE CHARACTERISTICS:

(A) LENGTH: 81
(B) TYPE: nucleic acid
(C) STRANDEDNESS: single
(D) TOPOLOGY: linear (xi) SEQUENCE DESCRIPTION: SEQ ID NO:18:

ATCCGCCTGA TTAGCGATAC TGACAATGAG TCAAGTCGCG TGCTCCCCTG    50

CTGTTGACTT GAGCAAAATC ACCTGCAGGG G    81

(2) INFORMATION FOR SEQ ID NO:19:

(i) SEQUENCE CHARACTERISTICS:
    (A) LENGTH: 81
    (B) TYPE: nucleic acid
    (C) STRANDEDNESS: single
    (D) TOPOLOGY: linear (xi) SEQUENCE DESCRIPTION: SEQ ID NO:19:

ATCCGCCTGA TTAGCGATAC TCGGGCCCCT GATTAACGCG CGCTGCCCCT    50

CGGGTGACTT GAGCAAAATC ACCTGCAGGG G    81

(2) INFORMATION FOR SEQ ID NO:20:

(i) SEQUENCE CHARACTERISTICS:
    (A) LENGTH: 81
    (B) TYPE: nucleic acid
    (C) STRANDEDNESS: single
    (D) TOPOLOGY: linear (xi) SEQUENCE DESCRIPTION: SEQ ID NO:20:

ATCCGCCTGA TTAGCGATAC TCGATATGAG CGTGAGCGTG CTTCCCTTGT    50

TGGTGNACTT GAGCAAAATC ACCTGCAGGG G    81

(2) INFORMATION FOR SEQ ID NO:21:

(i) SEQUENCE CHARACTERISTICS:
    (A) LENGTH: 81
    (B) TYPE: nucleic acid
    (C) STRANDEDNESS: single
    (D) TOPOLOGY: linear (xi) SEQUENCE DESCRIPTION: SEQ ID NO:21:

ATCCGCCTGA TTAGCGATAC TGTCTGTCAG ATTCATGCGT GCTCCCCCTT    50

CTGGTGACTT GAGCAAAATC ACCTGCAGGG G    81

(2) INFORMATION FOR SEQ ID NO:22:

(i) SEQUENCE CHARACTERISTICS:
    (A) LENGTH: 81
    (B) TYPE: nucleic acid
    (C) STRANDEDNESS: single
    (D) TOPOLOGY: linear (xi) SEQUENCE DESCRIPTION: SEQ ID NO:22:

ATCCGCCTGA TTAGCGATAC TCTGGAGCGT GCTGCCCCTA AAGGTGACTT    50

ACCAAGACTT GAGCAAAATC ACCTGCAGGG G    81

(2) INFORMATION FOR SEQ ID NO:23:

(i) SEQUENCE CHARACTERISTICS:
    (A) LENGTH: 81
    (B) TYPE: nucleic acid
    (C) STRANDEDNESS: single
    (D) TOPOLOGY: linear ( x i ) SEQUENCE DESCRIPTION: SEQ ID NO:23:

ATCCGCCTGA TTAGCGATAC TTAGCTACAC TATATGGCGT GCTCCCCCTG        50

TTCGTGACTT GAGCAAAATC ACCTGCAGGG G        81

( 2 ) INFORMATION FOR SEQ ID NO:24:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:24:

ATCCGCCTGA TTAGCGATAC TCTTGGCCCG TATTCGCGTG CTGTCCCCCT        50

GAGATGACTT GAGCAAAATC ACCTGCAGGG G        81

( 2 ) INFORMATION FOR SEQ ID NO:25:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:25:

ATCCGCCTGA TTAGCGATAC TGAACGTGCA GCCCCCCGAA ACGTGACTAG        50

CAANNNACTT GAGCAAAATC ACCTGCAGGG G        81

( 2 ) INFORMATION FOR SEQ ID NO:26:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:26:

ATCCGCCTGA TTAGCGATAC TGGATTTTTG TGCAAGCCCC CGAAAGCTGA        50

TNNNNNACTT GAGCAAAATC ACCTGCAGGG G        81

( 2 ) INFORMATION FOR SEQ ID NO:27:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:27:

ATCCGCCTGA TTAGCGATAC TACGTCAGGA CCCCTCATCG ATTTTCTTAA        50

GNNNNNACTT GAGCAAAATC ACCTGCAGGG G        81

( 2 ) INFORMATION FOR SEQ ID NO:28:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:28:

ATCCGCCTGA TTAGCGATAC TTTAGCAAAG GAGCCCCCGG ACTCAGATTA        50

CNNNNNACTT GAGCAAAATC ACCTGCAGGG G        81

( 2 ) INFORMATION FOR SEQ ID NO:29:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:29:

```
ATCCGCCTGA TTAGCGATAC TTGTTATAGT CCCCTGCCGC TGTTCTCGCG          50
GGATTNACTT GAGCAAAATC ACCTGCAGGG G                              81
```

( 2 ) INFORMATION FOR SEQ ID NO:30:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:30:

```
ATCCGCCTGA TTAGCGATAC TCAAGTCAAA TCCCCTGACA GGAATTCCTT          50
CCTGGAACTT GAGCAAAATC ACCTGCAGGG G                              81
```

( 2 ) INFORMATION FOR SEQ ID NO:31:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:31:

```
ATCCGCCTGA TTAGCGATAC TTGTTCAGTC CCCCTCTCAA GCTACTTTAC          50
TTTGTAACTT GAGCAAAATC ACCTGCAGGG G                              81
```

( 2 ) INFORMATION FOR SEQ ID NO:32:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:32:

```
ATCCGCCTGA TTAGCGATAC TAGCGAGCTT ATTAGAAGGA TAAACCGCCT          50
ANNNNNACTT GAGCAAAATC ACCTGCAGGG G                              81
```

( 2 ) INFORMATION FOR SEQ ID NO:33:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:33:

```
ATCCGCCTGA TTAGCGATAC TTGCTGGTCA TAGGTAAACA GCCCTGAGCT          50
AACAGAACTT GAGCAAAATC ACCTGCAGGG G                              81
```

( 2 ) INFORMATION FOR SEQ ID NO:34:

( i ) SEQUENCE CHARACTERISTICS:

( A ) LENGTH: 81
            ( B ) TYPE: nucleic acid
            ( C ) STRANDEDNESS: single
            ( D ) TOPOLOGY: linear ( x i ) SEQUENCE DESCRIPTION: SEQ ID NO:34:

ATCCGCCTGA TTAGCGATAC TCAGAAGGAT AAACTGTCCA GAACATGGAA           50

TATATCACTT GAGCAAAATC ACCTGCAGGG G                              81

( 2 ) INFORMATION FOR SEQ ID NO:35:

( i ) SEQUENCE CHARACTERISTICS:
            ( A ) LENGTH: 81
            ( B ) TYPE: nucleic acid
            ( C ) STRANDEDNESS: single
            ( D ) TOPOLOGY: linear ( x i ) SEQUENCE DESCRIPTION: SEQ ID NO:35:

ATCCGCCTGA TTAGCGATAC TATCGAGGTG ATCAGAAGGA TAAACCGCCG           50

GGGCCTACTT GAGCAAAATC ACCTGCAGGG G                              81

( 2 ) INFORMATION FOR SEQ ID NO:36:

( i ) SEQUENCE CHARACTERISTICS:
            ( A ) LENGTH: 81
            ( B ) TYPE: nucleic acid
            ( C ) STRANDEDNESS: single
            ( D ) TOPOLOGY: linear ( x i ) SEQUENCE DESCRIPTION: SEQ ID NO:36:

ATCCGCCTGA TTAGCGATAC TCTAAACGGT GAAGGGTCTT TGCAGATGAA           50

CAANNNACTT GAGCAAAATC ACCTGCAGGG G                              81

( 2 ) INFORMATION FOR SEQ ID NO:37:

( i ) SEQUENCE CHARACTERISTICS:
            ( A ) LENGTH: 81
            ( B ) TYPE: nucleic acid
            ( C ) STRANDEDNESS: single
            ( D ) TOPOLOGY: linear ( x i ) SEQUENCE DESCRIPTION: SEQ ID NO:37:

ATCCGCCTGA TTAGCGATAC TTTAGCAAAG TAGAAGCCGG TTAGAAGACC           50

TAGAACACTT GAGCAAAATC ACCTGCAGGG G                              81

( 2 ) INFORMATION FOR SEQ ID NO:38:

( i ) SEQUENCE CHARACTERISTICS:
            ( A ) LENGTH: 81
            ( B ) TYPE: nucleic acid
            ( C ) STRANDEDNESS: single
            ( D ) TOPOLOGY: linear ( x i ) SEQUENCE DESCRIPTION: SEQ ID NO:38:

ATCCGCCTGA TTAGCGATAC TTTAGCAAAG TTGAAGCCGG ACTAACAAGC           50

TCTACGACTT GAGCAAAATC ACCTGCAGGG G                              81

( 2 ) INFORMATION FOR SEQ ID NO:39:

( i ) SEQUENCE CHARACTERISTICS:
            ( A ) LENGTH: 79
            ( B ) TYPE: nucleic acid
            ( C ) STRANDEDNESS: single
            ( D ) TOPOLOGY: linear ( x i ) SEQUENCE DESCRIPTION: SEQ ID NO:39:

ATCCGCCTGA TTAGCGATAC TGGGCTCAAG CTTGAGCGCG GCTCTCCACC    50

TACGACTTGA GCAAAATCAC CTGCAGGGG    79

( 2 ) INFORMATION FOR SEQ ID NO:40:

( i ) SEQUENCE CHARACTERISTICS:
  ( A ) LENGTH: 81
  ( B ) TYPE: nucleic acid
  ( C ) STRANDEDNESS: single
  ( D ) TOPOLOGY: linear ( x i ) SEQUENCE DESCRIPTION: SEQ ID NO:40:

ATCCGCCTGA TTAGCGATAC TTGTCGGGTG GCTTTAGCAG AGACAATATG    50

CATTNNACTT GAGCAAAATC ACCTGCAGGG G    81

( 2 ) INFORMATION FOR SEQ ID NO:41:

( i ) SEQUENCE CHARACTERISTICS:
  ( A ) LENGTH: 81
  ( B ) TYPE: nucleic acid
  ( C ) STRANDEDNESS: single
  ( D ) TOPOLOGY: linear ( x i ) SEQUENCE DESCRIPTION: SEQ ID NO:41:

ATCCGCCTGA TTAGCGATAC TCTATAACCA GGTTTCGGGT GCTTTAGCAA    50

ANNNNNACTT GAGCAAAATC ACCTGCAGGG G    81

( 2 ) INFORMATION FOR SEQ ID NO:42:

( i ) SEQUENCE CHARACTERISTICS:
  ( A ) LENGTH: 81
  ( B ) TYPE: nucleic acid
  ( C ) STRANDEDNESS: single
  ( D ) TOPOLOGY: linear ( x i ) SEQUENCE DESCRIPTION: SEQ ID NO:42:

ATCCGCCTGA TTAGCGATAC TGGGAGGGAG GGAGGGCCGT AGCTAATTAG    50

GATCAAACTT GAGCAAAATC ACCTGCAGGG G    81

( 2 ) INFORMATION FOR SEQ ID NO:43:

( i ) SEQUENCE CHARACTERISTICS:
  ( A ) LENGTH: 81
  ( B ) TYPE: nucleic acid
  ( C ) STRANDEDNESS: single
  ( D ) TOPOLOGY: linear ( x i ) SEQUENCE DESCRIPTION: SEQ ID NO:43:

ATCCGCCTGA TTAGCGATAC TACGCGTGCT GCCCCTAAAG GCGATTGTCG    50

GATGTTACTT GAGCAAAATC ACCTGCAGGG G    81

( 2 ) INFORMATION FOR SEQ ID NO:44:

( i ) SEQUENCE CHARACTERISTICS:
  ( A ) LENGTH: 81
  ( B ) TYPE: nucleic acid
  ( C ) STRANDEDNESS: single
  ( D ) TOPOLOGY: linear ( x i ) SEQUENCE DESCRIPTION: SEQ ID NO:44:

ATCCGCCTGA TTAGCGATAC TTACGTGAGC GTGCTGTCCC CTAAAGGTGA    50

TACGTCACTT GAGCAAAATC ACCTGCAGGG G    81

( 2 ) INFORMATION FOR SEQ ID NO:45:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:45:

```
ATCCGCCTGA TTAGCGATAC TCTGGAGCGT GCTGCCCCTA AAGGTGACTT        50
ACCAAGACTT GAGCAAAATC ACCTGCAGGG G                            81
```

( 2 ) INFORMATION FOR SEQ ID NO:46:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:46:

```
ATCCGCCTGA TTAGCGATAC TCGCGTGCTG CCCCTTAAGG TGATGGTGTA        50
TATTCCACTT GAGCAAAATC ACCTGCAGGG G                            81
```

( 2 ) INFORMATION FOR SEQ ID NO:47:

( i ) SEQUENCE CHARACTERISTICS:
        ( A ) LENGTH: 79
        ( B ) TYPE: nucleic acid
        ( C ) STRANDEDNESS: single
        ( D ) TOPOLOGY: linear ( x i ) SEQUENCE DESCRIPTION: SEQ ID NO:47:

```
ATCCGCCTGA TTAGCGATAC TTCTCCGACT CAAAGCGCGT GCTCCCCTCC        50
GGTGACTTGA GCAAAATCAC CTGCAGGGG                               79
```

( 2 ) INFORMATION FOR SEQ ID NO:48:

( i ) SEQUENCE CHARACTERISTICS:
        ( A ) LENGTH: 82
        ( B ) TYPE: nucleic acid
        ( C ) STRANDEDNESS: single
        ( D ) TOPOLOGY: linear ( x i ) SEQUENCE DESCRIPTION: SEQ ID NO:48:

```
ATCCGCCTGA TTAGCGATAC TCGTATAGGT CCCCTGCCGC TAAACAGCGC        50
CGCGGTAACT TGAGCAAAAT CACCTGCAGG GG                           82
```

( 2 ) INFORMATION FOR SEQ ID NO:49:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:49:

```
ATCCGCCTGA TTAGCGATAC TGCCAGGTCC CCTGTAATTA GACGGAAACT        50
ACCTGTACTT GAGCAAAATC ACCTGCAGGG G                            81
```

( 2 ) INFORMATION FOR SEQ ID NO:50:

( i ) SEQUENCE CHARACTERISTICS:

(A) LENGTH: 81
            (B) TYPE: nucleic acid
            (C) STRANDEDNESS: single
            (D) TOPOLOGY: linear (xi) SEQUENCE DESCRIPTION: SEQ ID NO:50:

ATCCGCCTGA TTAGCGATAC TGCCAGGACC CCTGTAATCT GGCGTATTTC     50

CCTGTTACTT GAGCAAAATC ACCTGCAGGG G     81

(2) INFORMATION FOR SEQ ID NO:51:

(i) SEQUENCE CHARACTERISTICS:
            (A) LENGTH: 81
            (B) TYPE: nucleic acid
            (C) STRANDEDNESS: single
            (D) TOPOLOGY: linear (xi) SEQUENCE DESCRIPTION: SEQ ID NO:51:

ATCCGCCTGA TTAGCGATAC TCGCCAGTAC CCCTGTAAGT GGGCGGAAAC     50

TCTAGTACTT GAGCAAAATC ACCTGCAGGG G     81

(2) INFORMATION FOR SEQ ID NO:52:

(i) SEQUENCE CHARACTERISTICS:
            (A) LENGTH: 81
            (B) TYPE: nucleic acid
            (C) STRANDEDNESS: single
            (D) TOPOLOGY: linear (xi) SEQUENCE DESCRIPTION: SEQ ID NO:52:

ATCCGCCTGA TTAGCGATAC TTCGTCAGGA CCCCTGTAAA CAGGCGGGAT     50

AATCTAACTT GAGCAAAATC ACCTGCAGGG G     81

(2) INFORMATION FOR SEQ ID NO:53:

(i) SEQUENCE CHARACTERISTICS:
            (A) LENGTH: 80
            (B) TYPE: nucleic acid
            (C) STRANDEDNESS: single
            (D) TOPOLOGY: linear (xi) SEQUENCE DESCRIPTION: SEQ ID NO:53:

ATCCGCCTGA TTAGCGATAC TGGGCCCTCA GCTTGAGCGC GGACTACATA     50

TTATCACTTG AGCAAAATCA CCTGCAGGGG     80

(2) INFORMATION FOR SEQ ID NO:54:

(i) SEQUENCE CHARACTERISTICS:
            (A) LENGTH: 81
            (B) TYPE: nucleic acid
            (C) STRANDEDNESS: single
            (D) TOPOLOGY: linear (xi) SEQUENCE DESCRIPTION: SEQ ID NO:54:

ATCCGCCTGA TTAGCGATAC TGGGCCCTCA GCTTGAGCGC GGAATCACTA     50

AGATACACTT GAGCAAAATC ACCTGCAGGG G     81

(2) INFORMATION FOR SEQ ID NO:55:

(i) SEQUENCE CHARACTERISTICS:
            (A) LENGTH: 81
            (B) TYPE: nucleic acid
            (C) STRANDEDNESS: single
            (D) TOPOLOGY: linear ( x i ) SEQUENCE DESCRIPTION: SEQ ID NO:55:

ATCCGCCTGA TTAGCGATAC TGGGCCCTCA GCTAGAGCCG GATTAAACAG　　　　50

TCTTCAACTT GAGCAAAATC ACCTGCAGGG G　　　　81

( 2 ) INFORMATION FOR SEQ ID NO:56:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:56:

ATCCGCCTGA TTAGCGATAC TTATTTGCCC TTGCAGGCCG CAGGAGTGCT　　　　50

AGCAGTACTT GAGCAAAATC ACCTGCAGGG G　　　　81

( 2 ) INFORMATION FOR SEQ ID NO:57:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:57:

ATCCGCCTGA TTAGCGATAC TCAGGCGTTA GGGAAGGGCG TCGAAAGCAG　　　　50

GGTGGGACTT GAGCAAAATC ACCTGCAGGG G　　　　81

( 2 ) INFORMATION FOR SEQ ID NO:58:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:58:

ATCCGCCTGA TTAGCGATAC TCAGGCGCCG GGGGGGTGGG AATACAGTGA　　　　50

TCAGCGACTT GAGCAAAATC ACCTGCAGGG G　　　　81

( 2 ) INFORMATION FOR SEQ ID NO:59:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:59:

ATCCGCCTGA TTAGCGATAC TCAGGCCTTG GGCGGGCCGG GACAATGGAG　　　　50

AGATTTACTT GAGCAAAATC ACCTGCAGGG G　　　　81

( 2 ) INFORMATION FOR SEQ ID NO:60:

( i ) SEQUENCE CHARACTERISTICS:
        ( A ) LENGTH: 80
        ( B ) TYPE: nucleic acid
        ( C ) STRANDEDNESS: single
        ( D ) TOPOLOGY: linear ( x i ) SEQUENCE DESCRIPTION: SEQ ID NO:60:

ATCCGCCTGA TTAGCGATAC TAGCCAGTCA AGTTAATGGG TGCCATGCAG　　　　50

AAGCAACTTG AGCAAAATCA CCTGCAGGGG　　　　80

( 2 ) INFORMATION FOR SEQ ID NO:61:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:61:

```
ATCCGCCTGA TTAGCGATAC TAATCGGCCT TGTTTCGGGG TGCTTTAGCA        50
GAGGAAACTT GAGCAAAATC ACCTGCAGGG G                            81
```

( 2 ) INFORMATION FOR SEQ ID NO:62:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:62:

```
ATCCGCCTGA TTAGCGATAC TCAGGGTGCC GCTCAATTCT GGGTGCCTTG        50
CAGAAGACTT GAGCAAAATC ACCTGCAGGG G                            81
```

( 2 ) INFORMATION FOR SEQ ID NO:63:

( i ) SEQUENCE CHARACTERISTICS:
        ( A ) LENGTH: 79
        ( B ) TYPE: nucleic acid
        ( C ) STRANDEDNESS: single
        ( D ) TOPOLOGY: linear ( x i ) SEQUENCE DESCRIPTION: SEQ ID NO:63:

```
ATCCGCCTGA TTAGCGATAC TCCAGCGGTG GCATCACGCG GACTTACTCT        50
AGCAACTTGA GCAAAATCAC CTGCAGGGG                               79
```

( 2 ) INFORMATION FOR SEQ ID NO:64:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:64:

```
ATCCGCCTGA TTAGCGATAC TTTAGCAAAG TTGAAGCCGG ACTAACAAGC        50
TCTACGACTT GAGCAAAATC ACCTGCAGGG G                            81
```

( 2 ) INFORMATION FOR SEQ ID NO:65:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:65:

```
ATCCGCCTGA TTAGCGATAC TCTAGCAGAG TAGAAGCCGG ACGATATATC        50
GATGATACTT GAGCAAAATC ACCTGCAGGG G                            81
```

( 2 ) INFORMATION FOR SEQ ID NO:66:

( i ) SEQUENCE CHARACTERISTICS:

( A ) LENGTH: 81
( B ) TYPE: nucleic acid
( C ) STRANDEDNESS: single
( D ) TOPOLOGY: linear ( x i ) SEQUENCE DESCRIPTION: SEQ ID NO:66:

```
ATCCGCCTGA TTAGCGATAC TGGACTCCCA GTTGATGCGC GGTCTTTATC        50
ACCTCCACTT GAGCAAAATC ACCTGCAGGG G                            81
```

( 2 ) INFORMATION FOR SEQ ID NO:67:

( i ) SEQUENCE CHARACTERISTICS:
( A ) LENGTH: 81
( B ) TYPE: nucleic acid
( C ) STRANDEDNESS: single
( D ) TOPOLOGY: linear ( x i ) SEQUENCE DESCRIPTION: SEQ ID NO:67:

```
ATCCGCCTGA TTAGCGATAC TAAGCTCTTA GTTGATGCGC GGTCAAAATT        50
TAAGCTACTT GAGCAAAATC ACCTGCAGGG G                            81
```

( 2 ) INFORMATION FOR SEQ ID NO:68:

( i ) SEQUENCE CHARACTERISTICS:
( A ) LENGTH: 81
( B ) TYPE: nucleic acid
( C ) STRANDEDNESS: single
( D ) TOPOLOGY: linear ( x i ) SEQUENCE DESCRIPTION: SEQ ID NO:68:

```
ATCCGCCTGA TTAGCGATAC TGAAGCTCTT TTAGTGATGC GTGGACCAGT        50
CCCCTTACTT GAGCAAAATC ACCTGCAGGG G                            81
```

( 2 ) INFORMATION FOR SEQ ID NO:69:

( i ) SEQUENCE CHARACTERISTICS:
( A ) LENGTH: 81
( B ) TYPE: nucleic acid
( C ) STRANDEDNESS: single
( D ) TOPOLOGY: linear ( x i ) SEQUENCE DESCRIPTION: SEQ ID NO:69:

```
ATCCGCCTGA TTAGCGATAC TGGGCTCCAG CTTGAGCGGC GACTTAATTG        50
GTTATTACTT GAGCAAAATC ACCTGCAGGG G                            81
```

( 2 ) INFORMATION FOR SEQ ID NO:70:

( i ) SEQUENCE CHARACTERISTICS:
( A ) LENGTH: 80
( B ) TYPE: nucleic acid
( C ) STRANDEDNESS: single
( D ) TOPOLOGY: linear ( x i ) SEQUENCE DESCRIPTION: SEQ ID NO:70:

```
ATCCGCCTGA TTAGCGATAC TGATATACTT ATTACTTCGC ACGGCTAACC        50
AGACCACTTG AGCAAAATCA CCTGCAGGGG                              80
```

( 2 ) INFORMATION FOR SEQ ID NO:71:

( i ) SEQUENCE CHARACTERISTICS:
( A ) LENGTH: 81
( B ) TYPE: nucleic acid
( C ) STRANDEDNESS: single
( D ) TOPOLOGY: linear
```

( x i ) SEQUENCE DESCRIPTION: SEQ ID NO:71:

ATCCGCCTGA TTAGCGATAC TCAGAAGGAT AAACTGTCCA GAACTTGGAA     50

TATATCACTT GAGCAAAATC ACCTGCAGGG G     81

( 2 ) INFORMATION FOR SEQ ID NO:72:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:72:

ATCCGCCTGA TTAGCGATAC TCTCGAGGTG ATCAGAAGGA TAAACCGCCG     50

GGGCCTACTT GAGCAAAATC ACCTGCAGGG G     81

( 2 ) INFORMATION FOR SEQ ID NO:73:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( x i ) SEQUENCE DESCRIPTION: SEQ ID NO:73:

GGUCCGAAGU GCAACGGGAA AAUGCACU     28

( 2 ) INFORMATION FOR SEQ ID NO:74:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( x i ) SEQUENCE DESCRIPTION: SEQ ID NO:74:

GTCCCTGTTC GGGCGCCA     18

( 2 ) INFORMATION FOR SEQ ID NO:75:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO:75:

CAGGGACAAG CCCGCGGUGA CGAUCUCUAA     30

( 2 ) INFORMATION FOR SEQ ID NO:76:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:76:

ATCCGCCTGA TTAGCGATAC TCGGAAGGAT ATAGTGTCTA CAACTACGGC     50

TACGTCACTT GAGCAAAATC ACCTGCAGGG G     81

( 2 ) INFORMATION FOR SEQ ID NO:77:

( i ) SEQUENCE CHARACTERISTICS:
        ( A ) LENGTH: 81

(B) TYPE: nucleic acid
(C) STRANDEDNESS: single
(D) TOPOLOGY: linear (xi) SEQUENCE DESCRIPTION: SEQ ID NO:77:

ATCCGCCTGA TTAGCGATAC TCAGACGGCG AGTCGGCCTA GCACGTGGAC 50

GATTTCACTT GAGCAAAATC ACCTGCAGGG G 81

(2) INFORMATION FOR SEQ ID NO:78:

(i) SEQUENCE CHARACTERISTICS:
(A) LENGTH: 81
(B) TYPE: nucleic acid
(C) STRANDEDNESS: single
(D) TOPOLOGY: linear (xi) SEQUENCE DESCRIPTION: SEQ ID NO:78:

ATCCGCCTGA TTAGCGATAC TCGGAAGGAT ATACTGTCTA GAACTTGGAA 50

AGTGTCACTT GAGCAAAATC ACCTGCAGGG G 81

(2) INFORMATION FOR SEQ ID NO:79:

(i) SEQUENCE CHARACTERISTICS:
(A) LENGTH: 81
(B) TYPE: nucleic acid
(C) STRANDEDNESS: single
(D) TOPOLOGY: linear (xi) SEQUENCE DESCRIPTION: SEQ ID NO:79:

ATCCGCCTGA TTAGCGATAC TCAGAAGGAT AAACCGTCCG GGACTTGCAA 50

TGAATAACTT GAGCAAAATC ACCTGCAGGG G 81

(2) INFORMATION FOR SEQ ID NO:80:

(i) SEQUENCE CHARACTERISTICS:
(A) LENGTH: 81
(B) TYPE: nucleic acid
(C) STRANDEDNESS: single
(D) TOPOLOGY: linear (xi) SEQUENCE DESCRIPTION: SEQ ID NO:80:

ATCCGCCTGA TTAGCGATAC TCGGAAGGAT AAACTGTCTA GAACTTGGAG 50

TCCATCACTT GAGCAAAATC ACCTGCAGGG G 81

(2) INFORMATION FOR SEQ ID NO:81:

(i) SEQUENCE CHARACTERISTICS:
(A) LENGTH: 81
(B) TYPE: nucleic acid
(C) STRANDEDNESS: single
(D) TOPOLOGY: linear (xi) SEQUENCE DESCRIPTION: SEQ ID NO:81:

ATCCGCCTGA TTAGCGATAC TCGGAAGGAT ACACTGTCTA GAACCTAGAG 50

TACGTCACTT GAGCAAAATC ACCTGCAGGG G 81

(2) INFORMATION FOR SEQ ID NO:82:

(i) SEQUENCE CHARACTERISTICS:
(A) LENGTH: 81
(B) TYPE: nucleic acid
(C) STRANDEDNESS: single
(D) TOPOLOGY: linear (xi) SEQUENCE DESCRIPTION: SEQ ID NO:82:

```
ATCCGCCTGA TTAGCGATAC TCAGGAGGAA CGACGGGACA GACCTTGGCA    50
TGTAGCACTT GAGCAAAATC ACCTGCAGGG G                         81
```

( 2 ) INFORMATION FOR SEQ ID NO:83:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:83:

```
ATCCGCCTGA TTAGCGATAC TCAGTCGGCC AAACTGTGAA GAACTCGGAC    50
GCCCTCACTT GAGCAAAATC ACCTGCAGGG G                         81
```

( 2 ) INFORMATION FOR SEQ ID NO:84:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:84:

```
ATCCGCCTGA TTAGCGATAC TCCGGAGGCT CAACTGTCCA GCAATTCGCA    50
CTCATCACTT GAGCAAAATC ACCTGCAGGG G                         81
```

( 2 ) INFORMATION FOR SEQ ID NO:85:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:85:

```
ATCCGCCTGA TTAGCGATAC TCGGAAGGAT AAACTGTCTA GAACCACGAA    50
TTTCCCACTT GAGCAAAATC ACCTGCAGGG G                         81
```

( 2 ) INFORMATION FOR SEQ ID NO:86:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:86:

```
ATCCGCCTGA TTAGCGATAC TCAGAAGGAT AGGCTGCCTA GAGCTTGGAA    50
TTTAGGACTT GAGCAAAATC ACCTGCAGGG G                         81
```

( 2 ) INFORMATION FOR SEQ ID NO:87:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:87:

```
ATCCGCCTGA TTAGCGATAC TCGGAAGGAT AAACAGCCCT GAGCTTGGAA    50
GTCGTCACTT GAGCAAAATC ACCTGCAGGG G                         81
```

( 2 ) INFORMATION FOR SEQ ID NO:88:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:88:

```
ATCCGCCTGA TTAGCGATAC TCAGAAGGAT AAACTGTCTA GAACTTGGAA        50
TATATTACTT GAGCAAAATC ACCTGCAGGG G                            81
```

( 2 ) INFORMATION FOR SEQ ID NO:89:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:89:

```
ATCCGCCTGA TTAGCGATAC TCGGAAGGAT AAAGTGCCCA CAGCCTGGAA        50
TGTAACACTT GAGCAAAATC ACCTGCAGGG G                            81
```

( 2 ) INFORMATION FOR SEQ ID NO:90:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:90:

```
ATCCGCCTGA TTAGCGATAC TCAGTAGGAT AAACTGTCTA GAACGCGGAA        50
GATATGACTT GAGCAAAATC ACCTGCAGGG G                            81
```

( 2 ) INFORMATION FOR SEQ ID NO:91:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:91:

```
ATCCGCCTGA TTAGCGATAC TCAGAAGGAT AAACTGTCGA GAACCTCGAA        50
TATGTCACTT GAGCAAAATC ACCTGCAGGG G                            81
```

( 2 ) INFORMATION FOR SEQ ID NO:92:

( i ) SEQUENCE CHARACTERISTICS:
        ( A ) LENGTH: 56
        ( B ) TYPE: nucleic acid
        ( C ) STRANDEDNESS: single
        ( D ) TOPOLOGY: linear ( x i ) SEQUENCE DESCRIPTION: SEQ ID NO:92:

```
ATCCGCCTGA TTAGCGATAC TCGGNAGGAN ANNCNGNNTN GNNCNNNGNN        50
NNCNNN                                                        56
```

( 2 ) INFORMATION FOR SEQ ID NO:93:

( i ) SEQUENCE CHARACTERISTICS:
        ( A ) LENGTH: 49

(B) TYPE: nucleic acid
(C) STRANDEDNESS: single
(D) TOPOLOGY: linear (x i) SEQUENCE DESCRIPTION: SEQ ID NO:93:

ATCCGCCTGA ATAGCGATAC TCAGAAGGAT AAACTGTCCA GAACTTGGA    49

(2) INFORMATION FOR SEQ ID NO:94:

(i) SEQUENCE CHARACTERISTICS:
(A) LENGTH: 30
(B) TYPE: nucleic acid
(C) STRANDEDNESS: single
(D) TOPOLOGY: linear (x i) SEQUENCE DESCRIPTION: SEQ ID NO:94:

ATCCGCCTGA ATAGCGATAC TCAGAAGGAT    30

We claim:

1. A purified and isolated non-naturally occurring DNA ligand to HIV-1 reverse transcriptase wherein said ligand is selected from the group consisting of the sequences set forth in SEQ ID NOS: 6–72 and 76–94.

* * * * *